(12) United States Patent
Sullivan

(10) Patent No.: US 8,525,533 B2
(45) Date of Patent: Sep. 3, 2013

(54) CONDUCTIVITY DETECTOR FOR FLUIDS

(75) Inventor: Thomas A. Sullivan, Pine Village, IN (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 408 days.

(21) Appl. No.: 12/883,611

(22) Filed: Sep. 16, 2010

(65) Prior Publication Data

US 2012/0068723 A1    Mar. 22, 2012

(51) Int. Cl.
*G01R 27/08* (2006.01)

(52) U.S. Cl.
USPC ........... 324/693; 324/439; 324/663; 324/692; 324/654; 73/61.44; 73/861; 73/861.05; 606/41; 506/1; 702/65

(58) Field of Classification Search
USPC ................. 324/600, 603–606, 663, 686, 688, 324/691, 692, 701, 439, 441, 448, 436, 654, 324/693; 73/861, 861.05
See application file for complete search history.

(56) References Cited

U.S. PATENT DOCUMENTS

| | | | |
|---|---|---|---|
| 2,599,413 | A | 9/1963 | Reichertz |
| 3,701,006 | A | 10/1972 | Volkel et al. |
| 3,993,945 | A | 11/1976 | Warmoth et al. |
| 4,740,755 | A | 4/1988 | Ogawa |
| 4,997,570 | A | 3/1991 | Polaschegg |
| 5,092,836 | A | 3/1992 | Polaschegg |
| 6,386,050 | B1 | 5/2002 | Yin et al. |
| 6,489,774 | B1 | 12/2002 | van de Goor et al. |
| 6,595,944 | B2 | 7/2003 | Balschat et al. |

(Continued)

FOREIGN PATENT DOCUMENTS

| | | |
|---|---|---|
| GB | 936 045 A | 4/1963 |
| WO | WO 02/40982 A1 | 5/2002 |
| WO | WO 2009/141431 A1 | 11/2009 |
| WO | WO 2010/016807 A1 | 2/2010 |

OTHER PUBLICATIONS

Laugere F. et al., "Design of an electronic interface for capacitively coupled four-electrode conductiveity detection in capillary electrophoresis microchip", Sensors and Actuators B: Chemical: International Journal Devoted to Research and Development of Physical and Chemical Transducers, Elsevier S.A., Switzerland, vol. 83, No. 103, Mar. 15, 2002 pp. 104-108.

(Continued)

*Primary Examiner* — Jermele M Hollington
*Assistant Examiner* — Son Le
(74) *Attorney, Agent, or Firm* — Leydig, Voit & Mayer, Ltd.

(57) ABSTRACT

A conductivity detector detects the electrical conductivity of a fluid under analysis for determining chemical or physical properties of the fluid that are related its electrical properties. Such conductivity detectors may find use in, for example, hemodialysis systems for analyzing the effectiveness of the hemodialysis treatment. In an aspect, to improve accuracy of the conductivity measurements, the detector utilizes four-wire resistance measurement methods. In another aspect, to avoid fouling or contamination of the electrodes, the detector utilizes capacitively-coupled contactless conductivity detection (C4D) methods so that the electrodes are physically unconnected to the fluid contained in a fluid chamber. In a possible further aspect, the fluid chamber may be a disposable component removable from the electrodes. The conductivity detector can include other features such as calibration circuits and features for electrically isolating the fluid under detection from the fluid in the rest of the system.

20 Claims, 15 Drawing Sheets

(56) References Cited

U.S. PATENT DOCUMENTS

| | | |
|---|---|---|
| 6,795,783 B2 * | 9/2004 | Kotlow et al. .................. 702/65 |
| 6,860,866 B1 | 3/2005 | Graf et al. |
| 7,629,797 B2 | 12/2009 | Tai et al. |
| 2004/0084372 A1 * | 5/2004 | Connell et al. ................ 210/646 |
| 2005/0109621 A1 | 5/2005 | Hauser et al. |
| 2009/0007642 A1 * | 1/2009 | Busby et al. ................. 73/61.44 |
| 2009/0036315 A1 * | 2/2009 | Labgold et al. ................... 506/1 |
| 2010/0010488 A1 * | 1/2010 | Kassab et al. ................... 606/41 |

OTHER PUBLICATIONS

International Search Report, PCT/US2011/051370, mailed Nov. 17, 2011.

* cited by examiner

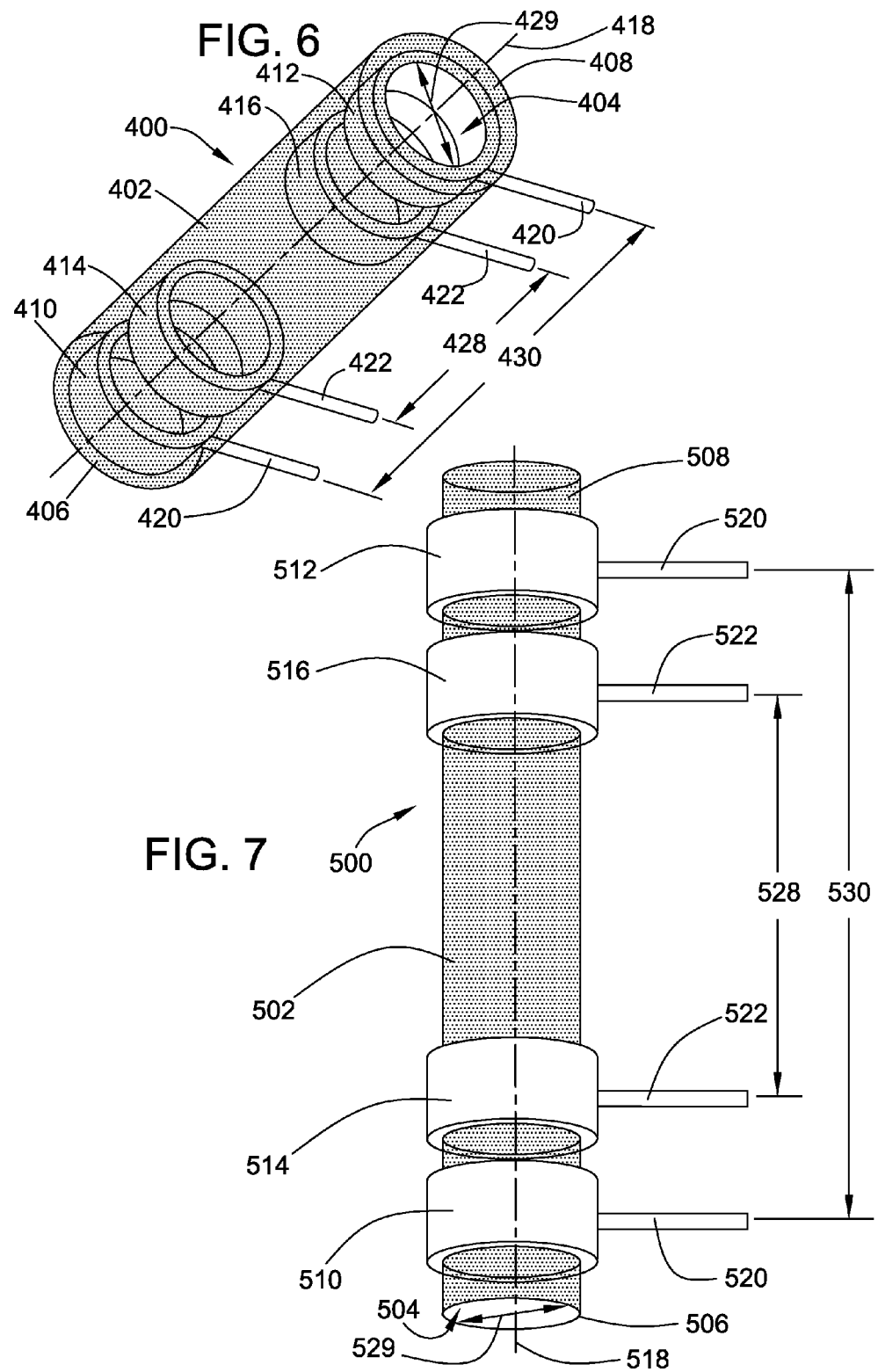

CONDUCTIVITY DETECTOR FOR FLUIDS

BACKGROUND OF THE INVENTION

In many medical, biological and chemical analytical applications, it is important to determine characteristics of fluids taken from a sample under study or consideration. For example, during hemodialysis to treat blood from a patient suffering kidney failure and related conditions, it is important to analyze the blood and/or dialysis fluid to determine the effectiveness of the treatment. Additionally, medical professionals may use information about the purity of the patient's blood being treated to form medical opinions and propose further therapy. Many various technologies have been developed for conducting such fluid analysis.

One such technology utilizes the electrical properties of the fluid under study to determine its purity and other data. All fluids have some measurable ability to conduct electricity and the purity or composition of the fluid may affect its conductivity. Hence, conductive sensing may be used to reveal information about the chemical composition of the fluid. Connecting a sample of the fluid into an appropriately designed electrical circuit enables analysis of the fluid's conductive properties and thus determination of it purity or composition and the effectiveness of dialysis filtration.

Conductivity analysis of fluids such as dialysis treated blood presents many technical challenges and difficulties. For example, while a sample of the fluid may be tested in isolation, it is often preferable to analyze the fluid in process. To accomplish this, it is necessary to incorporate the test circuit into the process such as making the test circuit part of the hemodialysis machine or system. Another complex issue involves the actual electrical coupling between the electrical circuit and the fluid being analyzed. For example, electrodes can be disposed into a channel through which the test fluid is directed. This design, however, may lead to fouling and contamination of the electrodes by the test fluid. Conversely, and especially when the test circuit is reused on multiple occasions, the electrodes may contaminate the fluid under test with traces of previously tested fluids.

To address contamination problems, various contactless designs for conductivity testing circuits have been designed and incorporated in fluid analysis systems. One such contactless design utilizes the principles of capacitive coupling between the electrode and the fluid so that the two do not have to be in direct physical contact. Applying an alternating current to an electrode placed proximate to a channel or test cell containing the fluid of interest will cause the electrode to capacitively couple with the fluid and enable gathering of electrical data regarding the fluid. Capacitively-coupled contactless conductivity detection (C4D) detectors are known and described in the prior art such as, for example, in International Publication No. WO 2010/016807 and U.S. Pat. No. 7,629,797. The sensitivity and accuracy of such detectors may be affected by the impedance and/or reactance associated with the circuit or system elements, the geometry and design of the electrodes and the test cell, and the material properties of the test fluid and the circuit or system elements. It is therefore necessary for a conductivity detector design to account these and other considerations to improve sensitivity and accuracy.

BRIEF SUMMARY OF THE INVENTION

The disclosure describes a conductivity detector for detecting the electrical conductivity of a fluid under analysis. The conductivity detector can be used to analyze fluid in any of various chemical, biological or medical applications such as, for example, a hemodialysis system. The conductivity detector can utilize a four-wire resistance measurement method in which two wires are coupled to a power source and induce a current in the fluid and two wires are coupled to a meter and sense the current induced in the fluid. In a particular aspect, the electrical resistance characteristic of the fluid will resist the induced current resulting in a voltage drop between the two wires coupled to the power source. By sensing the induced current and/or the voltage drop due to the fluid, the conductivity of the fluid can be determined from which information about the chemical or physical characteristics of the fluid can be deduced.

In one aspect, the conductivity detector can utilize capacitively-coupled contactless conductivity detection (C4D) methods to electrically couple with the fluid in a detector cell. The C4D design can include electrodes that are physically separated from the fluid by, for example, disposing the electrodes about a fluid chamber in which the fluid is contained. When a voltage is applied to an electrode, an electric charge will build up in the electrode which thereby functions as one plate of a capacitor. A corresponding electric charge will build up in the fluid disposed in the fluid chamber near the electrode, thereby functioning as the other plate of a capacitor. When the charge is remove or alternates phases, the electric charge in the fluid will discharge through the rest of the fluid chamber, thereby inducing a current in the chamber.

In another aspect, utilizing the C4D design, the conductivity detector can be designed to utilize a disposable and replaceable fluid chamber. Because the electrodes do not make direct physical contact with the fluid, the electrodes can also be separate from the fluid chamber in which the fluid is contained. The fluid chamber can therefore be designed as a removable component of the conductivity detector and can be made from inexpensive plastic. In a further aspect, the conductivity detector can include a casing in which the fluid chamber can be removably accommodated. The electrode can be formed as part of the casing so that the electrodes are locationally fixed or aligned with respect to the fluid chamber contained therein.

In yet another aspect, the conductivity detector can include a calibration portion that enables calibration of the detector. The calibration portion can include electrical components that replicate the fluid in the fluid chamber and the electrodes disposed about the fluid chamber. The power source and voltmeter can be selectively coupled to either the electrodes about the fluid chamber or to the calibration portion. Conductivity measurements sensed from the fluid chamber can be compared to the known conductivity measurement from the calibration portion for periodic calibration of the conductivity detector.

An advantage of the conductivity detector described herein is that it can provide a more accurate measurement of the conductivity of a fluid. Another advantage is that the conductivity detector can utilize a contactless design to electrically communicate with the fluid under analysis, thereby preventing fouling or contamination of the electrodes. A related advantage is that the fluid under analysis may be contained in a disposable fluid chamber, which can be replaced to further prevent contamination of the detector and/or fluid. These and other advantages and feature of the disclosure will become apparent from the following detailed description and accompanying drawings.

BRIEF DESCRIPTION OF THE DRAWINGS

FIG. 6 is a perspective view of a general representation of a conductivity cell configured for contacting and sensing a fluid directed through the cell.

FIG. 7 is an elevated view of a general representation of a conductivity cell configured for capacitively-coupled contactless conductivity detection of a fluid directed through the cell.

DETAILED DESCRIPTION

Figure 1:
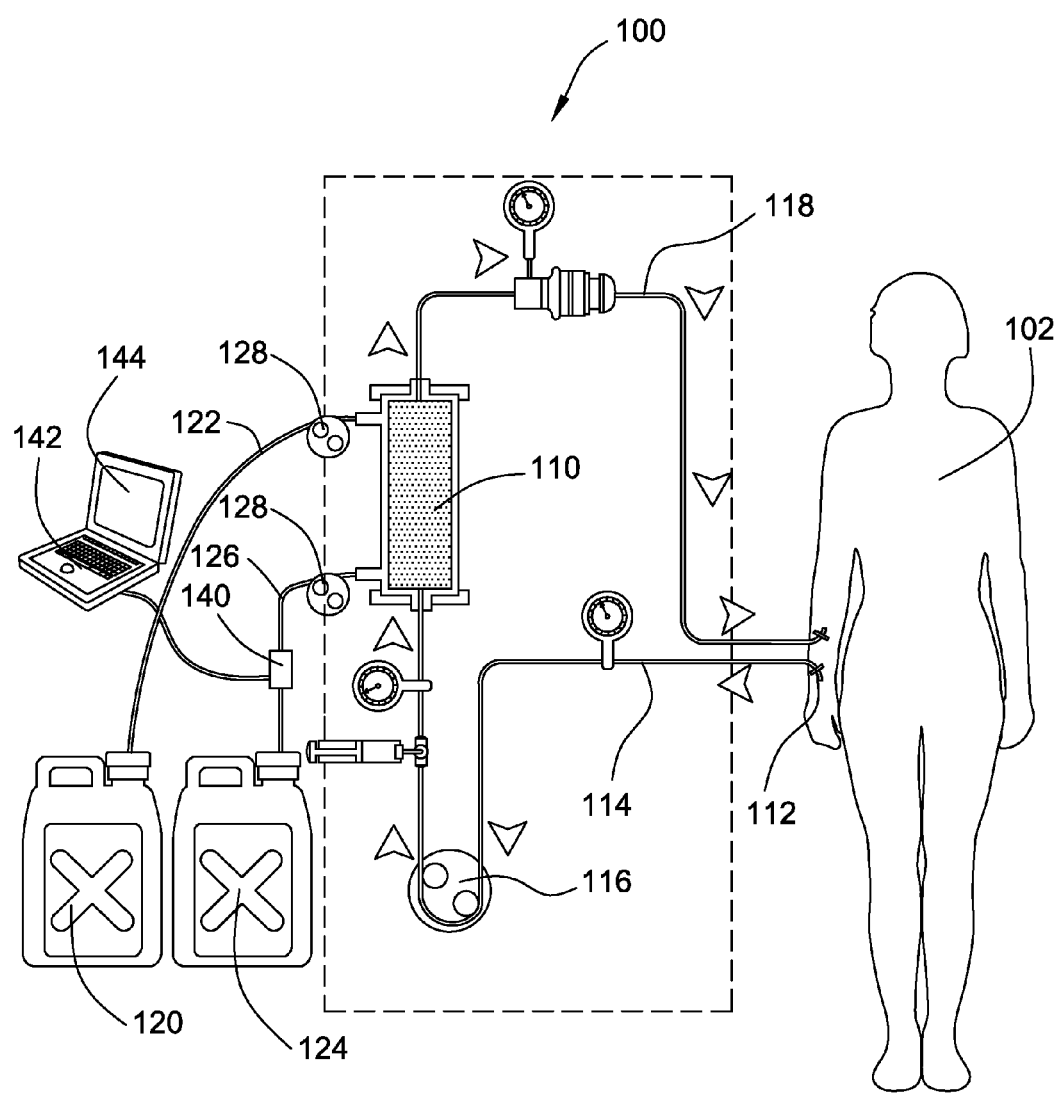
FIG. 1 is a schematic diagram of a hemodialysis system for treating blood removed from a patient with a dialysate fluid and that includes a conductivity detector for analyzing the dislysate.

Now referring to the drawings, wherein like reference numbers refer to like elements, there is illustrated in FIG. 1 an exemplary hemodialysis system 100 for filtration and removal of impurities from the blood of a patient 102. Although various aspects of the present disclosure are described with respect to hemodialysis treatment and systems, these aspects have applicability beyond hemodialysis and are not limited to hemodialysis, nor are the claims so limited unless explicitly stated. The hemodialysis system 100 includes a dialyzer 110 in which the filtration of blood is performed. The dialyzer 110 can be a cross-flow dialyzer in which blood flowing in one direction is separated from a dialysate fluid flowing in the opposite direction by a semi-permeable membrane. Through a process sometimes referred to as ultrafiltration, solutes and impurities in the blood can transfer across the membrane to the dialysate and directed out the dialyzer 110.

To direct blood from the patient 102 to the dialyzer 110, a catheter 112 inserted into the patient can be connected to the dialyzer via tubing or a removal line 114. To maintain the flow of blood from the patient 102 to the dialyzer 110, a pump 116 such as a rotary peristaltic pump can be disposed along the removal line 114 and applies a pressure to the system that directs or supplements blood flow in the appropriate direction. Filtered blood from the dialyzer 110 is returned to the patient 102 via a return line 118. Dialysate from a fresh dialysate container 120 can be communicated to the dialyzer 110 via a fresh dialysate line 122 and returned from the dialyzer to a used dialysate container 124 via a used dialysate line 126. One or more dialysate pumps 128 can be disposed along either or both the fresh dialysate line 124 and used dialysate line 126 for directing the dialysate to and from the respective containers and the dialyzer 110. Various pressure sensors and monitors can be disposed along the removal line 114 and return line 118 to monitor the flow of blood.

To monitor one or more characteristics, parameters and/or other data associated with the blood or other fluid being treated, the hemodialysis system 100 can include a conductivity detector 140 that is disposed in fluid communication with the system. In the illustrated embodiment of the hemodialysis system 100, the conductivity detector 140 is disposed downstream of the dialyzer 110 along the used dialysate line 126 so that it will receive and analyze used dialysate returning from the dialyzer 110, but in other embodiments the detector can be incorporated in other locations within the system. The conductivity detector 140 may be communicatively coupled to one or more other electrical devices 142 such as an electrical control unit or a computer for providing power and/or data analysis. To communicate the data to medical personal conducting the dialysis treatment, the electrical device 142 can in turn be communicatively linked with one or more user interface devices 144 such as an LCD screen or the like. In the illustrated embodiment, the electrical device 142 and the interface device 144 are shown to be a personal computer but in other embodiments, they could be part of a specialized dedicated counsel or unit.

Fluid Conductivity

The following background on fluid conductivity is intended to provide the reader with a better understanding of the operation and construction of the conductivity detector and other concepts described herein. However, it should be noted that the present disclosure and each of the claims included herein are not intended to be limited to any particular theories unless explicitly stated. Almost all fluids, and more particularly liquids, have or demonstrate some degree of electrical conductivity whereby the fluid will carry an electrical current between two spaced-apart electrodes. Hence, conductivity is the property or measure of the ability of the fluid to conduct an electric current, and the conductivity between spaced-apart electrodes may be measured in Siemens/cm. Conductivity is the reciprocal or inverse of resistivity, the property or measure of the resistance of the fluid to passage of an electrical current. Because most fluids are neither perfect conductors or perfect resistors, they will have some measurable degree of both conductivity and resistivity.

Conductivity ($\kappa$) and resistivity ($\rho$) can be given by the following equations respectively:

$$\kappa = S*L/A \quad (1)$$

$$\rho = \Omega*A/L \quad (2)$$

Wherein:

κ is the conductivity in S/cm;

ρ is the resistivity in Ω*cm;

A is the area of the sample in $cm^2$;

L is the length of the sample in cm;

S is the electrical conductance of the sample in S; and

Ω is the electrical resistance of the sample in Ω.

Figure 2:
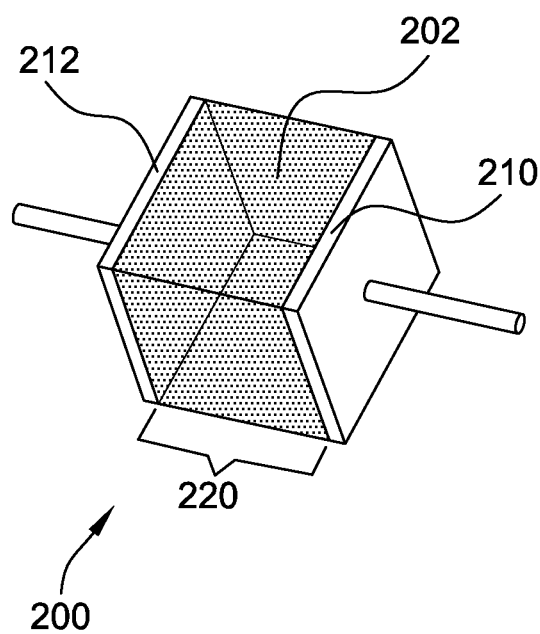
FIG. 2 is a schematic diagram of a conductivity cell for conductive analysis of a fluid.

Equations (1) and (2) can be applied to a test sample of a fluid such as is illustrated in FIG. 2. In FIG. 2, the fluid 202 under consideration can be disposed between a first metallic plate 210 and a parallel, spaced-apart second metallic plate 212. The first and second metallic plates 210, 212 can be electrically coupled to a power source so that the plates can function as electrodes. Although the plates illustrated in FIG. 2 are square, it will be appreciated that other shapes and sizes are contemplated. The structure depicted in FIG. 2 and similar structures are sometimes referred to as a conductivity cell 200 by those of skill in the art because they are used to measure the conductivity and/or resistivity of the fluid.

When a power source such as an AC or DC source is applied to the first and second plates 210, 212, the fluid 202 between them will partially resist the conduction of current between the plates or across the conductivity cell 200. Hence, the conductivity cell 200 behaves like a resistor. The resistance of the fluid 202 can be measured using Ohm's law, given by Equation (3), and measuring the voltage drop and/or current flow across the cell $$\text{Ohm's Law:} V = I * R \quad (3)$$

Wherein:

V is voltage;

I is current; and

R is resistance.

Applying Equations (1) and (2) for conductivity and resistivity to the conductivity cell 200 of FIG. 2, it will be appreciated that area A may represent the area of one of the plates 210, 212 and length L may represent the distance between the plates as indicated by bracket 220. The variables A and L can be predetermined during the design of the conductivity cell 200 by the designer. Hence, for a conductivity cell of predetermined dimensions with A and L pre-established, Equations (1) and (2) reduce to Equations (3) and (4) as follows:

$$\kappa = S * K_{cell} \quad (4)$$

$$\rho = \Omega / K_{cell} \quad (5)$$

Wherein $K_{cell}$ equals L/A and is referred to as the cell constant because it is calculated from predetermined, i.e. constant, area and length dimensions of the conductivity cell 200. For a given cell constant $K_{cell}$, it will be appreciated that resistance Ω for the fluid 202 may be determined from equation (3) and measurement of the voltage drop and/or current flow across the cell by appropriate meters. Equation (1) for conductivity is the reciprocal of equation (2) and therefore the conductivity of the fluid in the cell is readily solvable.

Four-Wire Resistance Measurement Method

Figure 3:
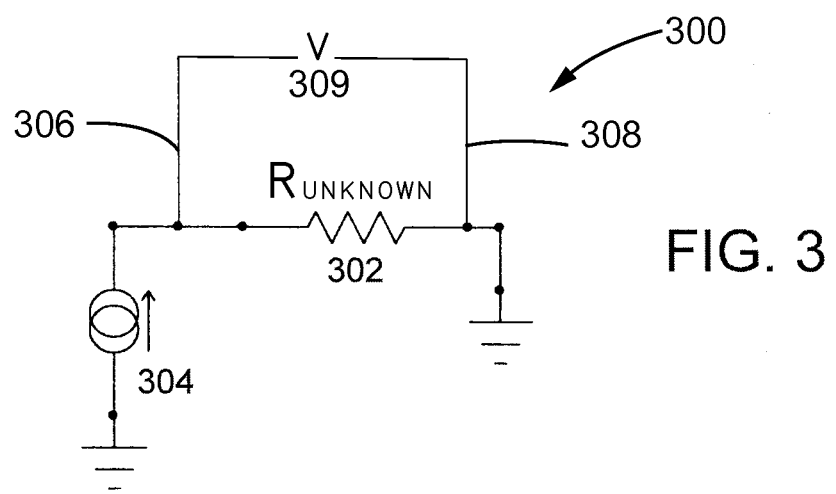
FIG. 3 is a schematic diagram depicting a simplified electrical representation of a detector circuit for performing conductive analysis.

To improve the accuracy of conductivity measurements of the fluid under sample, in one aspect of the present disclosure, the conductivity cell is configured to utilize, at least in part, known four-wire resistance measurement methods. Again, the following theoretical description is provided for a better understanding of the disclosure and is not intended to limit the claims unless explicitly stated. Referring to FIG. 3, there is illustrated a schematic representation of an electrical circuit such as a conductivity detector circuit 300 into which the conductivity cell has been incorporated. In the schematic diagram, the conductivity cell may be represented as an unknown resistance $R_{Unknown}$ 302, which as will be appreciated may represent the resistivity/conductivity of the fluid contained in the cell. In other words, unknown resistance $R_{Unknown}$ 302 is a value associated with the fluid and not a physical component such as a resistor.

The conductivity detector circuit 300 may also include a power source 304, such as a constant current source, which provides power to the circuit and which is electrically coupled to the unknown resistance $R_{Unknown}$ 302 representative of the conductivity cell. Current from the power source 304 can flow through the unknown resistance $R_{Unknown}$ 302 to ground. A meter, such as a ohmmeter, amp meter, or preferably a voltmeter 309, can be connected to the electrical circuit 300 by first and second meter lines 306, 308. If a voltmeter is used as the meter 309, it can measure the voltage drop across the unknown resistance $R_{Unknown}$ 302 to determine the conductivity of the fluid in the conductivity cell via Equations (1) and (2) above. The voltage drop across the unknown resistance $R_{Unknown}$ 302, which may vary with the fluid under analysis, serves as a signal indicative of the electrical and/or chemical properties of the material. In other embodiments, the current source may be replaced with a voltage source and the current through $R_{Unknown}$ is measured.

Figure 4:
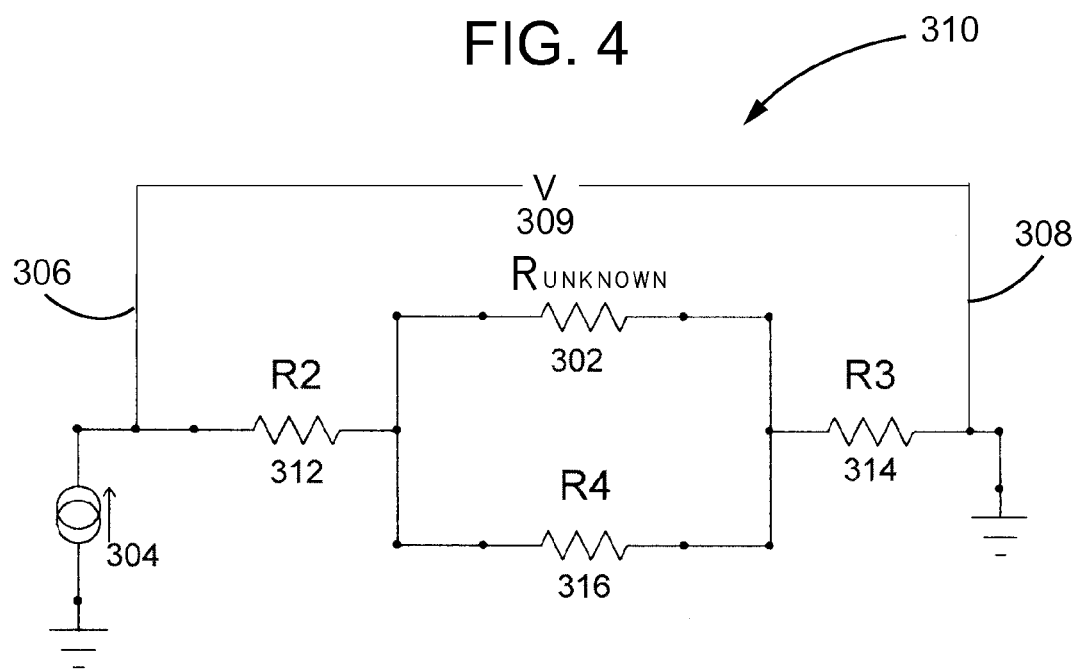
FIG. 4 is a schematic diagram of an improved electrical representation of the detector circuit for performing conductive analysis.

However, the circuit schematic illustrated in FIG. 3 is not as accurate a representation of a detector circuit incorporating a conductivity cell as possible because it does not account for resistance provided by the terminals, leads and connections included in the detector circuit. A more accurate and detailed representation of a detector circuit 310 is illustrated in FIG. 4, which again incorporates the unknown resistance $R_{Unknown}$ 302 representative of the conductivity cell. Two new resistances R2 312 and R3 314 are introduced into this detector circuit 310 which represent the electrical resistance of the electrodes, which are the physical connections between the detector circuit and the conductivity cell the resistance inherent in the wires or leads from the electrodes to the power source 304. These resistances R2 312 and R3 314 are shown connected in series with the unknown resistance $R_{Unknown}$ 302. Additionally, in FIG. 4, a resistance R4 316, which is shown connected in parallel with the unknown resistance $R_{Unknown}$ 302, may represent the resistance of the material that the conductivity cell is physical made from. If the voltmeter 309 is connected via meter leads 306, 308 to the detector circuit 310 as shown in FIG. 4, it will measure the voltage drop and/or current flow due to resistances R2 312, R3 314 and R4 316 as well as the voltage drop and/or current flow across the unknown resistance $R_{Unknown}$ 302.

In theory, if resistances R2 312, R3 314, and R4 316 are known, it is possible to calculate the value of the unknown resistance $R_{Unknown}$ 302 using known formulas for adding resistance in series and parallel. In many practical systems, though, these resistances are also unknown. For example, where the detector circuit 310 incorporates a conductivity cell for analyzing fluids, fouling and contamination of the electrodes and cell material by the fluid may affect resistances R2 312, R3 314 and R4 316. The unknown and possibly variable values for the resistances R2 312, R3 314 and R4 316 may result in errors in determining the value of unknown resistance $R_{Unknown}$ 302.

Figure 5:
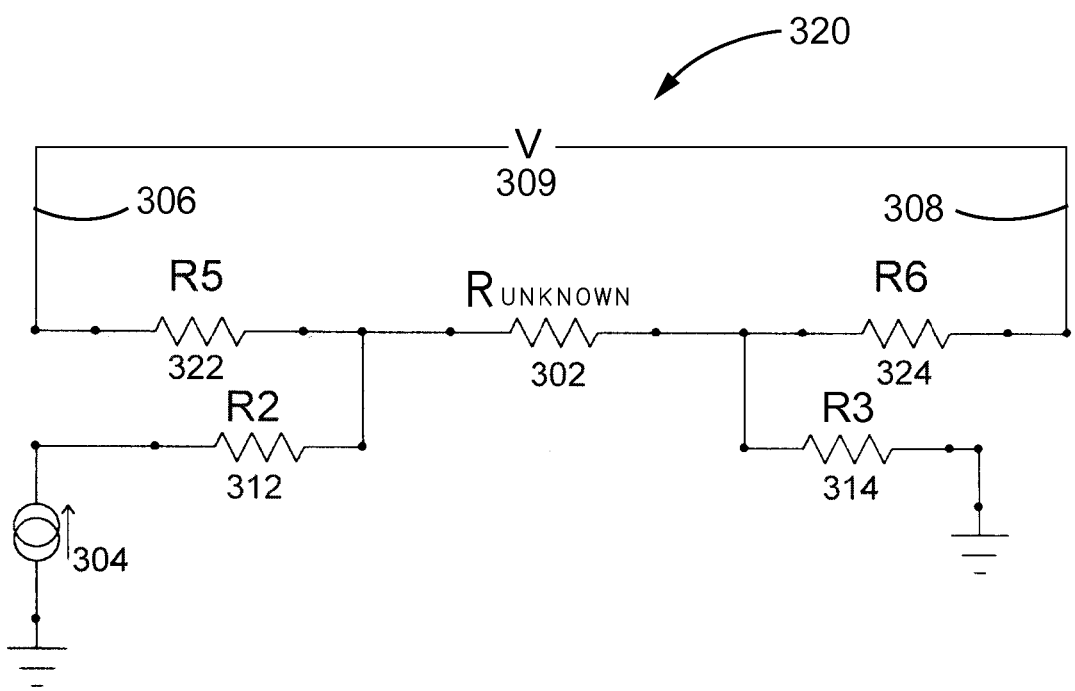
FIG. 5 is a schematic diagram of an electrical representation of an improved detector circuit for performing conductive analysis.

A solution to the foregoing problem is illustrated in FIG. 5, which depicts a detector circuit 320 that employs a four-wire resistance measurement method, sometimes referred to as the Kelvin measurement process. In this conductivity detector circuit 320, the voltmeter 309 and its associated meter lines 306, 308 are physically connected to, and preferably directly connected to, the electrodes on the conductivity cell represented by the unknown resistance $R_{Unknown}$ 302. Two new resistances, R5 322 and R6 324, are introduced which represent the resistance of the actual couplings or electrodes connecting the meter wires 306, 308 of the voltmeter 309 to the conductivity cell represent by the unknown resistance $R_{Unknown}$ 302. For purposes of this discussion, R4 316 will be ignored because the resistance of the cell material is often considered insignificant with respect to effect of resistances R2 312 and R3 314 and $R_{Unknown}$ 302.

In operation, the power source 304 will deliver constant current through resistance R2 312, the unknown resistance $R_{Unknown}$ 302, and resistance R3 314 to ground. However, the current diverted from the circuit 320 to the voltmeter 309 and thus through resistance R5 322 and R6 324, will be relatively small because the voltmeter requires relatively little current to operate. Because of Ohm's law (V=I*R) and the relatively small amount of current diverted to the voltmeter 309, the voltage drops caused by resistance R5 322 and R6 324 representing the physical coupling between the voltmeter and the conductivity cell are also relatively small, even if R5 and R6 are large. Hence, the voltmeter 309 will measure primarily the voltage drop only across unknown resistance $R_{Unknown}$ 302 thus enabling an accurate determination of the resistivity/ conductivity of the fluid in the conductivity cell. This is true regardless of the value or change in value of resistances R2 312 and R3 314 representing the couplings connected to the conductivity cell. Thus, using a detector circuit 320 applying the four-wire resistance measurement method to monitor the conductive cell provides a more accurate measurement of the conductivity of the fluid in the cell.

In a further embodiment, the detector circuit utilizing the four-wire resistance measurement method may be configured to operate with alternating current ("AC") power. As will be appreciated by those of skill in the art, in addition to electrical resistance, the AC embodiment of the detector circuit will have to account for reactance (X), which is the opposition of the circuit components to the change in current inherent in the AC power source, and impedance (Z), which is the sum of reactance of all the circuit components. Reactance and thus impedance may arise from the capacitance and inductance properties of the circuit components under AC power. One possible simplistic approach is to largely ignore the spurious, parasitic and transmission effects caused by capacitance and inductance and to estimate impedance by the following equation:

$$Z = V_{mag}/I \quad (6)$$

Wherein:
Z is the impedance, measured in Ohms;
$V_{mag}$ is the voltage, measured in volts; and
I is the current, measured in Amps.

In this simplification, R2-R6 in the detector circuit 320 of FIG. 5 may be replaced by Z2-Z6 to account for reactance and impedance in the AC detector circuit. Because impedance is the sum of the reactance for each individual component in the circuit, value for the impedance will vary directly with variations in value of the reactance of each component.

The detector circuit may include other features to facilitate conductive sensing of the fluid. For example, because the current to the voltmeter must be relatively small, amplifiers and the like can be incorporated to increase the current to suitable levels for electronic data analysis and processing. Various adders, filters, converters, registers, buffers, and the like can also be incorporated for similar data analysis and storage purposes. Additionally, while a generic power source was described above, in various embodiments, the power source can be designed to facilitate data capture. For example, where alternating current is used, the frequency and waveform of the input current can be selected to provide a predetermined input signal to the unknown resistance resulting in an output signal measured by the voltmeter. The output signal can be further output to an oscilloscope or other instruments or data acquisition apparatuses for signal analysis. This enables various signal processing methods and facilitates data capture and analysis. These and various other analytical techniques are considered to fall within the scope of the disclosure.

Conductivity Cells

Referring to FIG. 6, there is illustrated an embodiment of a conductivity cell 400 for measuring the conductivity of a fluid which generally utilizes and implements the four-wire resistance measurement method described above or variations thereof. The conductivity cell 400 includes a hollow fluid chamber 402 delineating an interior bore or channel 404 for receiving and containing the fluid. In the illustrated embodiment, the hollow fluid chamber 402 is an elongated cylindrical tube that is disposed along a cylindrical axis line 418. However, in other embodiments, the fluid chamber could have other possible shapes such as curved. The illustrated fluid chamber 402 can be made from any suitable material that is permeable to electro-magnetic fields such as medical grade polymers and, more preferably, from medical grade polyvinyl chloride ("PVC"). The cylindrical fluid chamber 402 can have any suitable size but, in the present embodiment, is generally 11.5 cm long by 2.54 cm in diameter.

In operation, to measure the conductivity of a fluid, the fluid chamber 402 will be disposed in fluid communication with a fluid system such as the hemodialysis system described above so that fluids may enter the hollow interior of the fluid chamber. In some embodiments, the conductivity cell 400 may be disposed "in-line" to directly receive fluids that are part of the hemodialysis process. In such embodiments, the tubular fluid chamber 402 may be opened at its first end 406 and its second end 408 so that fluids can access, pass through and exit the interior channel 404. In other embodiments, the fluid chamber may be "isolated" or "dead-ended" so as to only receive and contain fluids removed from the fluid circuit in the hemodialysis system. In such embodiments, only the first end 406 may be opened and the second end 408 may be sealed closed. For present discussion purposes, the fluid chamber 402 may be consider "in-line" with the first end 406 designated as the upstream end and the second end 408 designed as the downstream end to indicate the direction of fluid flow through the interior channel 404. Fluid flow into the conductivity cell 400 may be continuous or intermittent.

To electrically connect the conductivity cell 400 with the detector circuit, a plurality of electrodes in the form of annular conducting rings are radially disposed about the interior channel 404 of the cylindrical fluid chamber 402. The conducting rings can be made of an electrically conductive material such as metal. In specifically, the rings include a first excitation ring 410 and a second excitation ring 412 that are disposed axially outward along the length of the fluid chamber 402 with the first excitation ring proximate the upstream end 406 and the second excitation ring proximate the downstream end 408. As used herein, "proximate" should be construed broadly and may include "near" or "towards" as well as "at." Also included are a first sense ring 414 and a second sense ring 416 that are disposed axially inward of the outer excitation rings 410, 412. However, in other embodiments, it is contemplated that the outward and inward positions of the excitation and sense rings may be reversed so that the sense rings are outward of the excitation rings. The first and second excitation rings 410, 414 and the first and second sense rings 414, 416 are axially aligned together along the axis line 418. The excitation rings 410, 412 can be in electrical communication with the power source of the detector circuit via wires or leads 420 while the sense rings 414, 416 can be connected to the voltmeter via wires or leads 422.

In operation, a power source applies a voltage to the outer excitation rings 410, 412, so that the fluid within the fluid chamber 402 can conduct a current between the excitation rings thereby completing the circuit. The applied voltage can be an alternating current with the first and second excitation rings 410, 412 being 180° out of phase with each other. With respect to the above described detector circuit in FIG. 5, it will be appreciated that, in this embodiment, the fluid inside the fluid chamber 402 represents the unknown resistance $R_{unknown}$. The sense rings 414, 416 connected to the voltmeter, because of their intermediate position between the first and second excitation rings 410, 412 along the axial length of the fluid chamber 402, will measure or sense the voltage drop in the fluid located between the first sense ring 414 and the second sense ring 416. Utilizing the four-wire resistance measuring method described above, the voltage drop enables determination of the resistivity/conductivity of the fluid.

For the illustrated geometry of the fluid chamber 402 in FIG. 6, the cell constant $K_{cell}$ in equations (4) and (5) equals the axial distance between the centers of the inner first and second sense electrodes 414, 416, designated by arrow 428 in FIG. 6, divided by the cross-sectional circular area of the interior channel 404 designated by arrow 429. These dimensions determine the volume of fluid within the fluid chamber 402 at a given time that is represented as the unknown resistance $R_{Unknown}$ in the detector circuit. Hence, the fluid volume can be determined by the design and size of the fluid chamber. If the fluid chamber dimensions change, the cell constant can be recalculated using new values for the length and area dimensions. To ensure that the first and second excitation rings 410, 412 are outward of the first and second sense rings 414, 416, the excitation rings can be axially spaced apart a second distance 430 in the axial direction that is larger than the first distance 428 between the sense rings. Because of the intermediate position of the sense rings 414, 416 between the outwardly disposed first and second excitation rings 410, 412 along the axial length of the fluid chamber 402, the sense rings are certain to capture the current or electrical signal induced in and propagating through the fluid between the excitation rings. Additionally, because the first and second excitation rings are located outwardly of the first and second sense rings, they provide some degree of protection to the sense rings from external noise and electromagnetic interference. Because the first and second sense rings 410, 412 are axially spaced from each other by axial distance 428, it is certain that there will be a volume of fluid within the fluid chamber between the sense electrodes in which a measurable voltage drop due to $R_{Unknown}$ occurs.

In the embodiment of the conductivity cell 400 illustrated in FIG. 6, the excitation rings 410, 412 and the sense rings 414, 416 can be embedded in the material of the fluid chamber walls such that the rings are exposed to the interior channel 404 and come into physical contact with the fluid therein to complete the electrical connection. However, physical contact may lead to corrosion or fouling of the electrodes and/or fluid. This may also present safety issues in applications where the fluid passing through the conductivity cell is to return to the patient or the voltages used are exceptionally high and the fluid presents an electrical shorting danger.

To address issues arising from physical contact with the fluid under analysis, FIG. 7 discloses a contactless design for the conductivity cell 500. In FIG. 7, the conductivity cell 500 again includes a cylindrical fluid chamber 502 with a hollow interior channel 504 that is opened at its first and second ends 506, 508 to allow fluid communication through the chamber. Electrodes in the form of conductive first and second excitation rings 510, 512 are disposed outwardly along the axial length of the fluid chamber 502 so that the first and second excitation rings are proximate the respective first and second ends 506, 508 of the fluid chamber. The first and second sense rings 514, 516 are disposed axially inward of the first and second excitation rings 514, 516 and are arranged so that the excitation rings and sense rings are axially aligned along axis line 518 of the conductivity cell 500. The excitation rings 510, 512 can be linked to the power source via wires 520 and the sense rings 514, 516 can be linked to the voltmeter via wires 522. The cell constant $K_{cell}$ for the conductivity cell 500 is a function of the axial distance between the centers of first and second sense rings 514, 516, indicated by arrow 528, and the mean inner diameter of the fluid chamber 502 through which the fluid is directed, indicated by arrow 529. The excitation rings 510, 512 can be spaced apart an axial second distance 530 that is greater than the axial first distance 528 between the sense electrodes 514, 516.

In contrast to the embedded design of FIG. 6, the annular electrode rings of FIG. 7 radially surround and encompass the exterior of the wall of the cylindrical fluid chamber 502 so that no direct contact between the fluid in the interior channel 504 and electrode rings occurs. To electrically detect fluid properties in the absence of direct contact between the electrodes and the fluid, the conductivity cell in FIG. 7 utilizes a capacitive coupling method. In a capacitively-coupled contactless detection (C4D) design, conductive excitation electrodes are positioned proximate to, but physically separated from, a material such as a fluid under analysis. When an AC current is applied to the electrode, it will simulate one plate of a capacitor and will have an electric charge build up within it. The material under analysis that is proximate to the electrode can simulate the opposite plate of the capacitor allowing a corresponding charge to build up within it. When the AC source changes phase, the electrode and fluid simulating the capacitor plates can discharge. If a sense electrode is in the vicinity of the excitation electrode and separated from it only by the material under analysis, the charge build up in the material will capactivitely cause a corresponding charge build up in the sense electrode. Hence, the material under analysis and the sense electrode simulate a second capacitor which will charge and discharge in accordance with the AC signal applied to the excitation electrode.

With reference to FIG. 7, the excitation ring 510 simulates one plate of the capacitor, the wall material of the fluid chamber 502 simulates the dielectric, and the fluid in the fluid chamber forms the other plate of the capacitor. Likewise, the fluid, the fluid chamber wall and the sense ring 514 simulate a second capacitor. Hence, the excitation ring 510, the fluid in the fluid chamber 502 and the sense ring 514 are capacitively coupled together forming a C4D structure. To incorporate the four-wire resistance measurement method, the second excitation ring 512 and the second sense ring 516, and the fluid surrounded by these rings, can also form another C4D structure. By way of capacitive coupling, a voltage applied to the outer first and second excitation rings 510, 512 will cause a current to be induced in and propagate across the axial length of the fluid chamber 502 which can be sensed by the innerwardly positioned first and second sense rings 514, 516. Through appropriate calibration and comparison with the applied voltage, the sense rings 514, 516 can be made sensitive to the voltage drop in the fluid therebetween. The voltage drop between the first and second sense rings 514, 516 can be used to determine the resistivity/conductivity of the fluid in the cell chamber 502.

Figure 8:
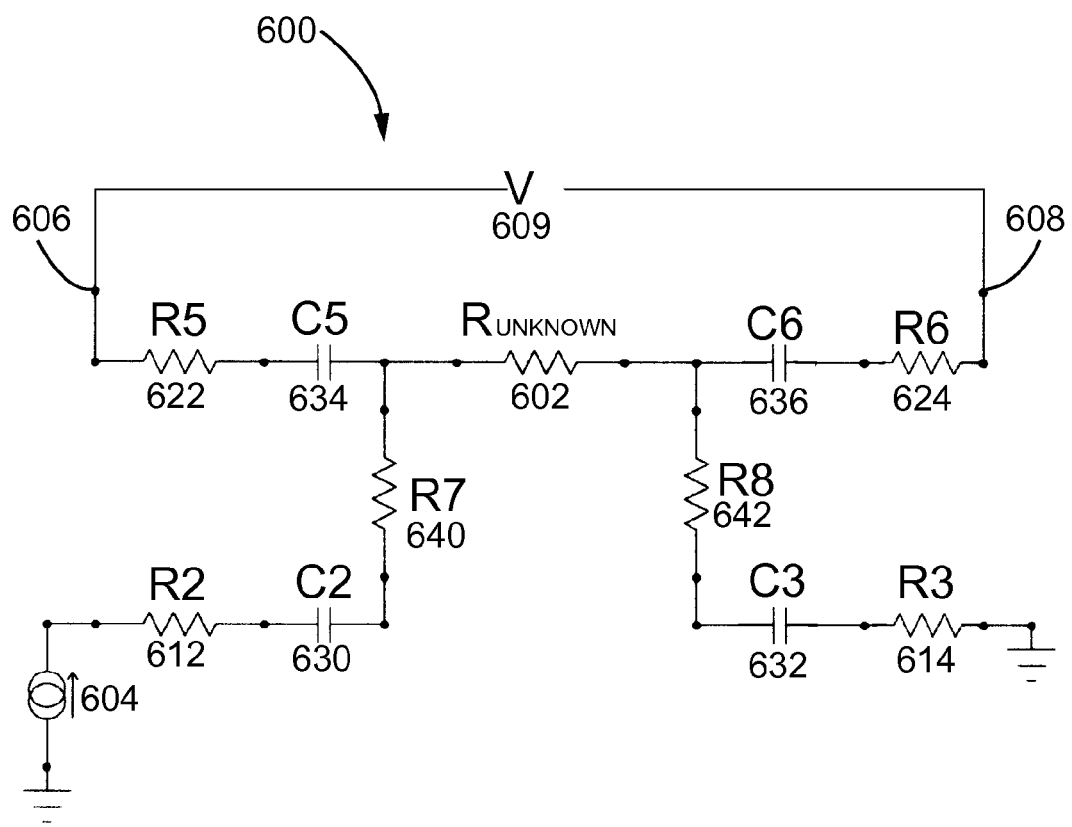
FIG. 8 is a schematic diagram of an electrical representation of a detector circuit for use in conjunction with a capacitively-coupled contactless conductivity cell such as is illustrated in FIG. 7.

Schematically, the conductivity cell 500 of FIG. 7 can be represented as the detector circuit 600 diagramed in FIG. 8. The unknown resistance $R_{Unknown}$ 602 continues to represent the resistance or impedance of the fluid in the conductivity cell. Links between the power source 604 through the conductivity cell to the ground or a return are represented by resistances R2 612 and R3 614, while links between the voltmeter 609 connected to the conductivity cell via meter links 606, 608 are represented by resistances R5 622 and R6 624. Capacitors are introduced to the schematic representation to represent the coupling between the electrode rings and the fluid in the cell. For example, capacitance C2 630 represents the capacitive coupling between the first excitation ring and the fluid within the conductivity cell. Likewise, capacitance C3 632 represents the capacitive coupling between the second excitation ring and the fluid, while capacitances C5 634 and C6 636 represent the couplings between the fluid and the first and second sense rings, respectively. Because there is a physical space or gap between the excitation rings and sense rings in the axial direction of the conductivity cell, two new resistances R7 640 and R8 642 are introduced. Referring to FIGS. 7 and 8, resistance R7 640 represents the resistance of the fluid located between the first excitation ring 510 and the first sense ring 514 that would not be part of the measured voltage drop between the first and second sense rings 514, 516. Resistance R8 642 likewise represents the voltage drop between the second excitation ring 512 and the second sense ring 516. Overall though, the four-wire architecture is substantially retained in the schematic representation illustrated in FIG. 8.

In operation, an AC power source is applied to the excitation rings represented by capacitances C2 630 and C3 632 that will capacitively couple with and propagate through the fluid between the excitation rings. This induced charge or signal in the fluid can couple with or be sensed by the sense rings represented by capacitances C5 634 and C6 636 and thereby registered or recorded on the voltmeter 609. The voltage drop between the first and second sense rings, represented by the unknown resistance $R_{Unknown}$ 602, is also measured by voltmeter 609. The voltage drop is dependent upon the impedance or conductive properties of the fluid and can be translated into information and data about the chemical and physical properties of the fluid. Experimentation can correlate the electrical and physical properties to enable analysis of the fluid.

Particular advantages may be obtained from capacitively coupling the conductivity cell to the detector circuit. For example, referring back to FIG. 7, the C4D design allows the fluid chamber 502 to be configured as a disposable part of the overall system. In particular, the fluid chamber 502 can be a cylindrical, thin-walled plastic tube that can be slidably inserted through the excitation rings 510, 512 and sense rings 514, 516 in the direction of axis line 518. The open first and second ends 506, 508 of the hollow fluid chamber 502 can be placed in fluid communication with the rest of the system to receive test fluid. After use, the fluid chamber 502 can be disconnected with the fluid conduit of the system, slidably removed from the excitation rings 510, 512 and sense rings 514, 514, and discarded. A new fluid chamber can replace the discarded fluid chamber. Hence, the excitation rings, the sense rings and the other circuit components of the detector circuit and all connections therebetween can be reused with only the inexpensive plastic fluid chamber being replaced.

Additionally, the distance 528 between the first and second sense rings 514, 516 can be rigidly fixed in the conductivity cell 500 in relation to the fluid chamber 502 so that the value of the cell constant $K_{cell}$ is consistently maintained and generally repeatable even as the fluid chambers are removed and replaced. The disposable design, further embodiments of which are described below, has important advantages in systems that involve medical, chemical or biological fluids because disposability promotes cleanliness and avoids contamination.

Referring to FIGS. 7 and 8, another possible advantage is that the detector circuit 600 can be configured to detect whether an insufficient amount of fluid is present in the fluid chamber 502, for example, due to gas bubble formation in the fluid circuit or an incompletely filled chamber. It is generally desirable that the fluid completely fill the fluid chamber and no gas bubbles form therein. For this reason, the fluid chamber 502 can be oriented vertically with its outlet directed upward to guide gas bubbles outward and the internal walls can be made relatively smooth to prevent bubble formation and adherence. In addition, a method can be utilized to detect an incompletely filled chamber. Referring to FIG. 8, if a large volume of gas is present in the fluid chamber, the resistance and/or impedance at $R_{Unknown}$ 602, and possibly resistances R7 640 and R8 642, will begin to rise towards infinity. This is because the volume of gas in the fluid chamber "opens" or breaks the detector circuit 600. The meter 609 can detect this increasing resistance and, if it rises above a predetermined threshold, the detector circuit 600 can determine the fluid chamber is not properly filled and reject the recently gathered data as an aberration. In some applications, such as medical ones, the detector circuit can also provide a warning or shut down the procedure if voids in the fluid might create a safety issue. Once the fluid begins to fill the fluid chamber again and the resistance and/or impedance at $R_{Unknown}$ 602 returns to normal levels, the detector circuit can return to collecting data.

To monitor for bubble formation overtime, the detector circuit can monitor for noise or a change in noise in the system. For example, bubble formation will cause rapid changes or spikes in the conductivity of the fluid in the fluid chamber over a short period of time which may quickly disappear when the bubbles collapse or exit the chamber. The data analysis equipment associated with the detector circuit can average the measured conductivity of the fluid in the detector cell over a period of time and thereby determine a steady-state or average fluid conductivity that accounts for bubbles forming and passing through the chamber. Instantaneous or nearly instantaneous measurements of conductivity of the fluid can be taken and compared to the average conductivity to determine the "noise" within the system. The level of noise can be used to assess if the system is operating effectively or not.

EXAMPLE 1

The following example serves to describe some of the considerations and operational characteristics of an embodiment of a conductivity cell designed in accordance with the foregoing teachings. To start, the capacitance of a parallel plate capacitor is given by the following equitation:

$$C = \epsilon_r \epsilon_o (A/d) \quad (7)$$

Wherein:
C is capacitance in farads;
$\epsilon_r$ is the dielectric constant;

$\in_o$ is the permittivity of free space, which equals 8.854×10$^{-12}$;

A is the plate area, in meter$^2$; and d is the distance between the electrode plates in meters.

Equation 7 may be applied to the fluid chamber having the dimensions described above, with a diameter of 2.54 cm and length of 11.5 cm. A dielectric constant of 3 can be assumed for the PVC plastic used for the fluid chamber material. The walls of the fluid chamber can be assumed to be 0.08 cm thick which will equate with dimension d in equation 7. The width of the electrode rings that encircle the fluid chamber can be assumed to be 1 cm, and the plate area can be determined as the circumferential area of the electrode rings. With these assumptions, Equation 7 gives a capacitance of 26 pico-farads for the above-described conductivity cell.

Because of the relatively low value of 26 pico-farads for capacitance, it will be appreciated that the capacitive coupling between the electrode rings and fluid is less than optimal. Where the fluid under test in the conductivity cell has a high conductivity, and therefore still functions as a good conductor, the low capacitance will not present much of a problem. However, if the fluid under test has a low conductivity, the capacitance and the cell constant $K_{cell}$ will have a more profound effect.

For example, capacitance and reactance are inversely proportional due to the equation:

$$X_c = 1/(2\Pi * F * C) \qquad (8)$$

Wherein:

$X_c$ is the reactance;

F is the AC frequency of the applied voltage; and

C is the capacitance.

Hence, the low value of capacitance means that the conductivity cell will have a high value of associated reactance and therefore a high impedance, i.e., apparent resistance, to alternating current, which is directly proportional to reactance. High impedance means that the detector circuit may be susceptible to cross-talk, electromagnetic interference, and other obstacles to measurement accuracy.

Also from Equation 8, it will be appreciated that the operating frequency of the detector circuit will effect the impedance of the conductivity cell. The choice of operating frequency may be application dependent. For example, in hemodialysis systems, AAMI standards permit operating frequencies up to 100 KHz as nerve and cardiac functions of the patients are less responsive to high frequencies. Conversely, though, high frequencies result in lower impedance values for the detector circuit, higher frequencies are more difficult to amplify and present additional disadvantages of cross-talk and interference. Other trade-offs will be apparent to those of skill in the art.

To reduce impedance of the detector circuit, it is therefore desirable to increase the coupling capacitance between the fluid and the ring electrodes. Increasing coupling capacitance may be accomplished by, for example, increasing the width of the coupling rings to increase plate area in Equation 7; increasing the diameter of the fluid chamber; using non-circular or complex geometries to increase electrode area; using thin walled chambers to decrease the plate distance in Equation 7; and embedding the electrode rings within the chamber wall to decrease plate distance in Equation 7. These considerations can be addressed in part by the additional embodiments described herein.

Conductivity Cell Casing

It will be appreciated from the foregoing that the location, dimensions, and arrangement of the fluid chamber, electrode rings and other components of the system will affect the electrical characteristics and therefore the sensitivity of the conductivity cell and the detector circuit. To improve sensitivity and repeatability of the conductivity cell, it is therefore desirable to make the cell with accurate precision and mechanically stability. When use of a disposable fluid chamber is desired, though, a competing desire is simplification and reduced precision of the chamber design to lower costs. To resolve these competing considerations, in an aspect, there is disclosed a conductivity cell casing that can removably accommodate or house a disposable fluid chamber during fluid analysis.

Figure 9:
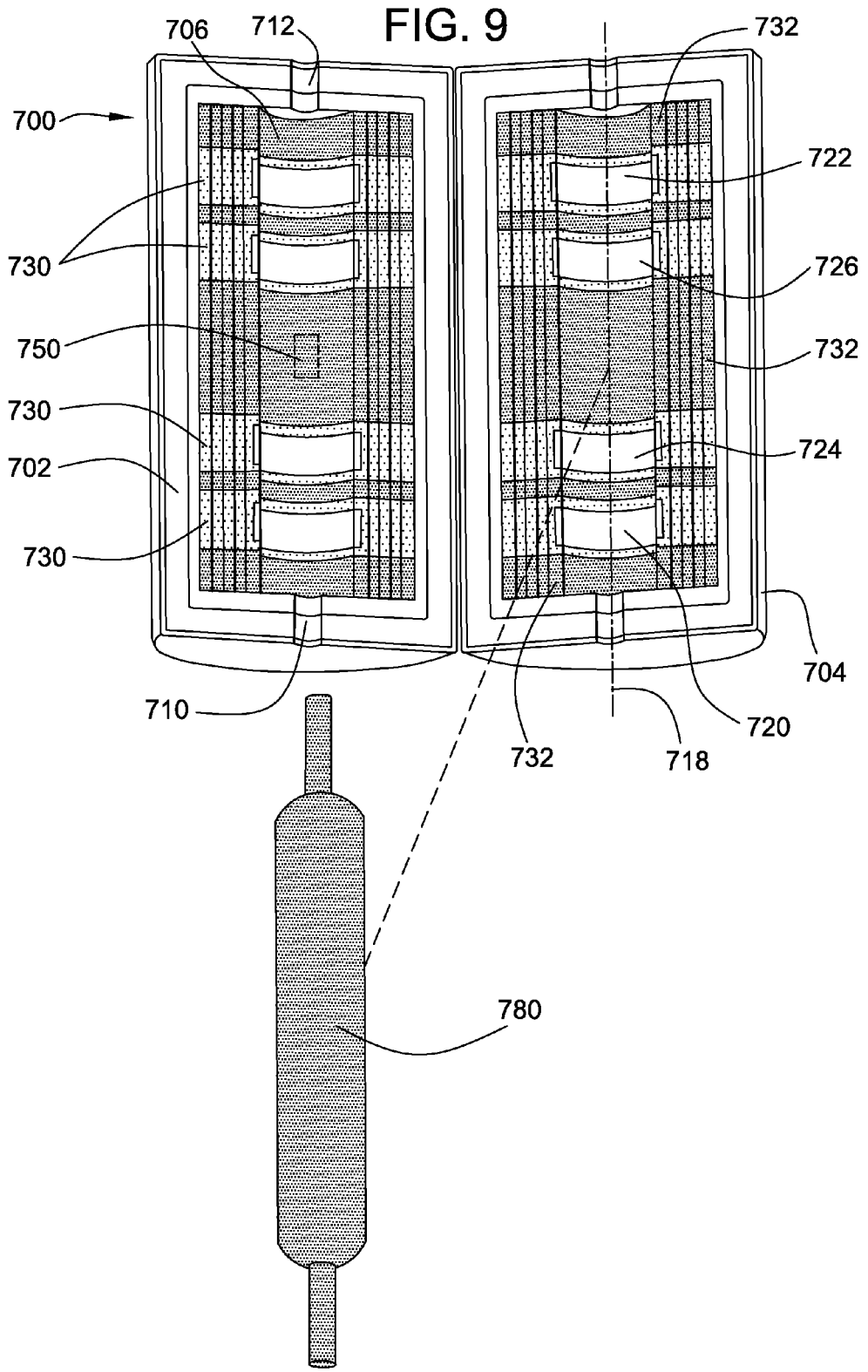
FIG. 9 is a perspective view of a cell casing for accommodating and facilitating capacitive coupling with a fluid chamber through which fluid under analysis is directed.
Figure 10:
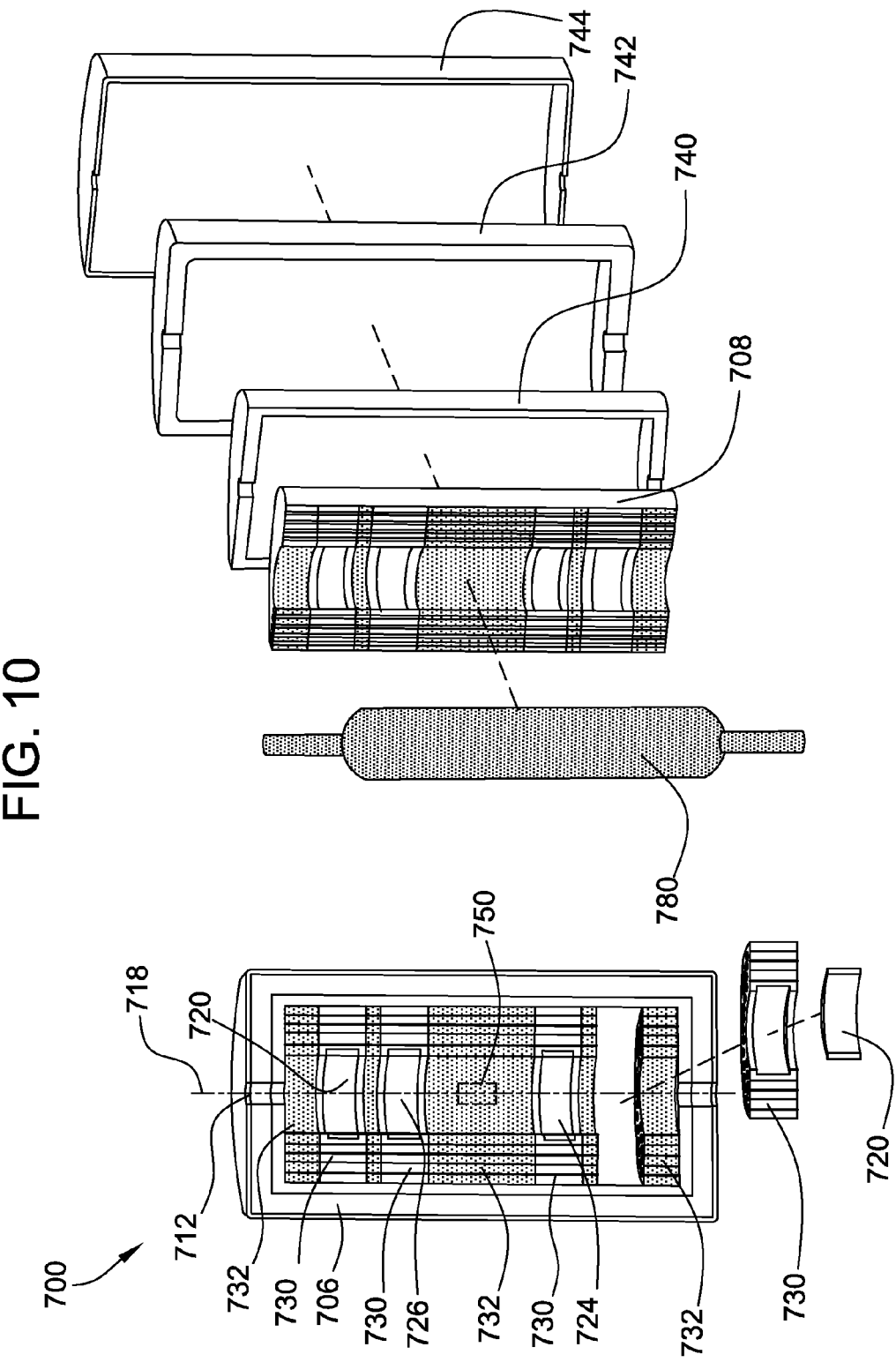
FIG. 10 is a perspective assembly view of the casing of FIG. 9.

For example, referring to FIGS. 9 and 10, there is illustrated an example of a cell casing 700 that has an elongated, generally cylindrical shape or form. The disposable fluid chamber 780 to be housed in the casing 700 is also illustrated and can have a smaller but similar cylindrical shape with a smaller diameter and axial length. Fluid communication with the internally retained fluid chamber 780 can be established by an inlet port 710 and an exit port 712 disposed into the opposite ends of the cylindrical casing 700. The inlet port 710 and exit port 712 are aligned along the cylindrical axis line 718 of the casing 700. To access the interior of the casing 700 that will contain the disposable fluid chamber 780, the casing is separated along its axial length into complementary first and second half cylinders 702, 704. The separate half cylinders 702, 704 of the casing 700 may be joined by latches or hinges that allow them to articulate with respect to one another to open and close the cell casing 700.

To accommodate the fluid chamber 780, each of the first and second half cylinders 702, 704 have disposed therein a respective interior contour or slot 706, 708 which, when the first and second half cylinders are placed adjacent one another, can form a cavity of a shape complementary to the shape of the fluid chamber. In the embodiments utilizing a disposable fluid chamber 780, the fluid chamber can be formed from thin-walled, extrude polyvinyl chloride (PVC) or polyethylene that demonstrate a degree of flexibility, elasticity or resilience so as to have a malleable quality. The first and second interior slots 706, 708 can be sized to produce a slight interference fit with the flexible or malleable fluid chamber 780 so that, when accommodated in the cavity, the fluid chamber is pressed or forced into a shape predetermined by the cavity. Hence, the disposable fluid chamber 780 can be rigidly held with repeatable accuracy in the casing 700. The final dimensions of the fluid chamber are thereby determined in part by the shape of the cavity. This also allows the disposable fluid chamber 780 to be manufactured with less precise, lower quality techniques to further reduce the expense of the fluid chamber.

To accurately align the electrode rings about the disposable fluid chamber 780, the electrode rings can be formed as an integral part of the conductivity cell casing 700. For example, the first and second half cylinders 706, 708 can include a plurality of semi-annular bands of a conductive material such as stainless steel or iron nickel alloys such as Invar. In particular, first and second semi-annular bands 720, 722 can be disposed at approximately the opposite ends of the axial length of each half cylinder 706, 708 of the cylindrical casing 700 and can correspond to the excitation rings. Conductive third and fourth semi-annular bands 724, 726 can also be disposed in each half cylinder 702, 704 axially inward of the first and second bands 720, 722 but still are axially spaced apart from each other to correspond to the sense rings. When the first and second half cylinders 702, 704 are moved adjacent to each other, the first and second semi-annular bands 720, 722 will encircle the disposable fluid chamber 780 and contact each other to form the complete annular excitation rings. Likewise, the third and fourth semi-annular bands 724, 726 can move together to form the annular sense rings. Various leads, wires or traces can establish electrical communication between the semi-annular bands and the exterior of the casing 700.

To electrically isolate the semi-annular bands from each other, the casing 700 can include a corresponding number of semi-annular band holders 730. The band holders 730 can be sized and shaped to receive and fix the semi-annular bands 720, 722, 724, 726 about the diameter of the disposable fluid chamber 780 and can be made from any suitable insulative material. To properly locate the band holder 730 along the axial length of the casing 700, and thus to align the excitation and sense rings at the proper axial locations about the disposable fluid chamber 780, the casing can include one or more isolators 732. The isolators 732 can also have a semi-annular shape and can space apart the band holders 730. Use of the isolators to fix the axial spacing and distance between the semi-annular bands 720, 722, 724, 726 improves the consistency of the cell constant $K_{cell}$ which is in part dependent upon these dimensions. Fixing the spacing between the annular bands thus enable repeatability between disposable fluid chambers. The isolators 732 also axially align each of the semi-annular bands in the first half cylinder 702 with the corresponding semi-annular band in the second half cylinder 704 to ensure that accurate annular rings with good electrical conductivity are formed when the half cylinders are adjacent to each other and the casing is closed.

To function as electrical isolators, the band holders and the isolators can be made from a suitable non-conducting material such as plastic like polyetheretherketone ("PEEK") and polyamide-imides marketed under the tradename Torlon® by Solvay Advanced Polymers L.L.C. Suitable ceramics for the band holders and insulators include glass-mica. To counter the possible effect of thermal expansion of the components and to thereby maintain alignment of the components of the cell casing, it is preferable that both the conductive semi-annular bands 720, 722, 724, 726 and the non-conductive band holders 730 and insulators 732 be made from materials that have a low coefficient of thermal expansion. Additionally, the various components can be cast or machined to improve their alignment accuracy.

To maintain all the components in mutual alignment and provide further shielding from electro-magnetic interference ("EMI"), the band holders 730 and isolators 732 can be disposed in a cast iron or ferrite shield 740. The cast iron or ferrite shield 740 may also be formed as a semi-cylindrical structure with a bored out interior for receiving and containing the band holders and isolators in rigid alignment. The cast iron or ferrite material will shield the conductivity cell components from internal and external EMI. To prevent shorting and further isolate the casing 700, the shield 740 can be disposed into an insulative shell 742 which is further surrounded with an aluminum shell 744 to provide another barrier of EMI shielding. The insulative shell 742 also provides thermal insulation to maintain a consistent temperature of the fluid under analysis, since fluid temperature has a significant effect on conductivity. Hence, the conductivity cell casing 700 and its components can provide both capacitive coupling with the fluid chamber and the fluid therein and can shield the conductivity cell from EMI.

In a possible further aspect of the disclosure, to enable temperature monitoring of the fluid undergoing analysis, the cell casing 700 can include a window indicated by dashed lines 750 disposed into it. The window 750 enables radiation from an infrared sensor to access the interior cavity of the casing 700 during operation so as to impinge upon and reflect from the fluid therein. Infrared sensors known in the art utilize similar techniques to measure the temperature of a substance. The temperature of a fluid affects its conductivity and therefore temperature is often taken into account when performing conductivity analysis. For example, analytical equations may utilize the "specific conductivity" of a fluid, which is based on the fluid's "absolute conductivity" corrected by a temperature dependent function. In the illustrated embodiment of the cell casing 700, the window 750 is disposed mid-length of the first half cylinder 706 to be aligned with the portion of the interior cavity in which current is induced into the fluid. The window 750 can include an infrared-transparent material such as polyethylene to allow passage of the infrared radiation. Thus, measurement of the fluid temperature in the conductivity cell is enabled. In other embodiments, the window and infrared sensor may be disposed at other locations along the fluid path rather than in the cell casing.

Electrical Isolation of the Conductivity Cell

Figure 11:
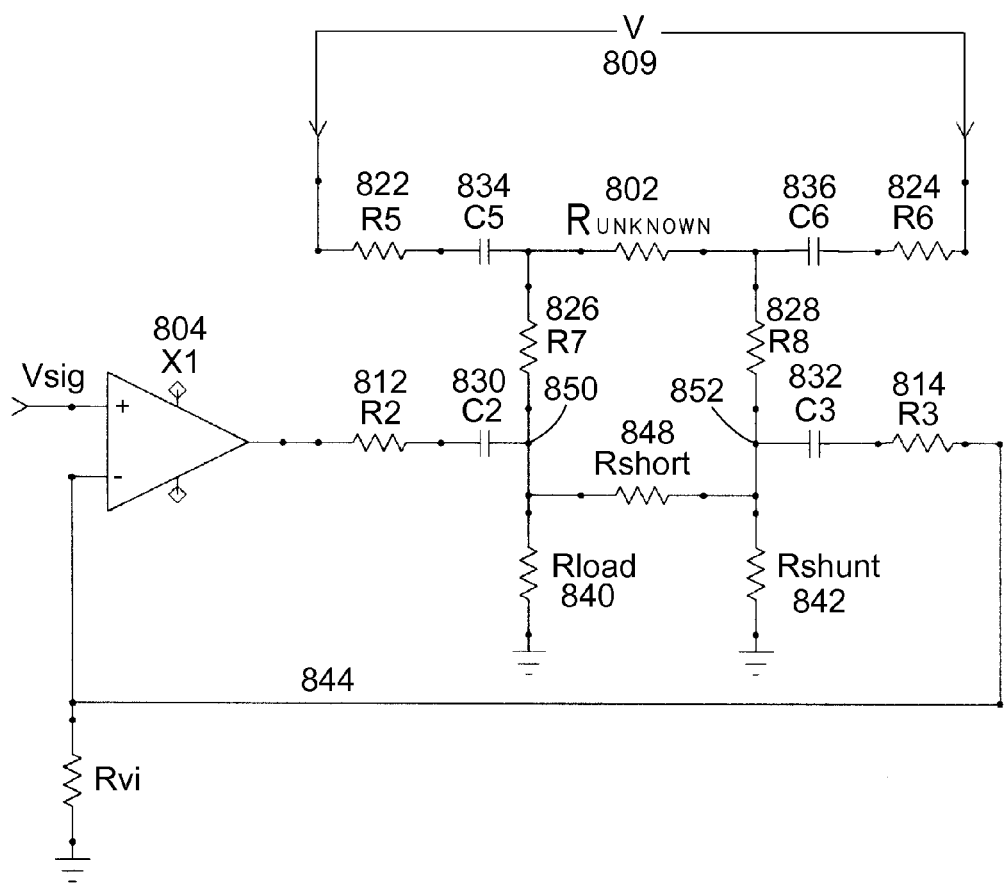
FIG. 11 is a schematic diagram of an electrical representation of a detector circuit for the purpose of illustrating the effects of parasitic current and current leakage.

As will be appreciated by those of skill in the art, detector circuits such as those described herein are subject to current leakage, parasitic currents, EMI and the like because the fluid under analysis becomes part of the conductive circuit while at the same time that fluid maybe still flowing in a continuous flow system such as a hemodialysis system. In other words, the fluid cannot be effectively isolated from itself. Thus, use of fluid as a conductor has latent and unintended repercussions as that fluid reenters the system, which may affect other fluid entering the detector circuit for analysis. Referring to FIG. 11, these problems can be illustrated schematically.

In FIG. 11, similar to FIG. 8, the electric symbols toward the top half of the diagram represent the physical components of a C4D detector circuit utilizing the four-wire resistance measurement method. Hence, the fluid under analysis in the fluid chamber is represented by the unknown resistance $R_{Unknown}$ 802. Resistances R2 812 and R3 814 represent the resistance of the leads to the excitation rings coupled to the fluid in the fluid chamber and which are represented by capacitors C2 830 and C3 832. Likewise, resistances R5 822 and R6 824 represent the resistance from the leads to the voltmeter 809 respectively, while capacitances C5 834 and C6 836 represent the capacitive couplings between the sense electrode rings and the fluid in the fluid chamber. Resistances R7 826 and R8 828 represent fluid in the fluid chamber between the excitation and sense rings that offers conductivity resistance that is not necessarily measured by the detector circuit. In the schematic of FIG. 11, the power source 804 is represented by an operational amplifier but any suitable alternating current power source for delivering an alternating current signal could be utilized.

In FIG. 11, three new resistances are presented that represent parasitic currents or current leakage in the detector circuit that diverts or detracts from the current supplied from the power source 804. $R_{load}$ 840 represents the diversion or shunting of current from the fluid, represented in part by capacitor C2 830, to ground rather than to the fluid under analysis. This could be current lost to ground through the fluid flowing through the system. In a detector circuit utilizing an operational amplifier or the like as a power source 804, it will be appreciated that some current or signal, or feedback, must be returned to the input of the operational amplifier as represented by feedback line 844. Resistance $R_{shunt}$ 842 represents current source error arising from this feedback in these particular detector circuits. Resistance $R_{short}$ 848 represents any current that may short through the remainder of the fluid system, via one cell port to the opposite cell port. Each of these current losses, represented by resistors $R_{load}$ 840, $R_{shunt}$ 842, and $R_{short}$ 848, are applied to or directed through node 850 and/or node 852, which represents the coupling between the first excitation ring and the fluid and the second excitation ring and the fluid respectfully. In this aspect of the disclosure, the parasitic current and leakage represented by resistances $R_{load}$ 840, $R_{shunt}$ 842, and $R_{short}$ 848 are eliminated or reduced in order to improved the accuracy of the conductivity cell.

Figure 12:
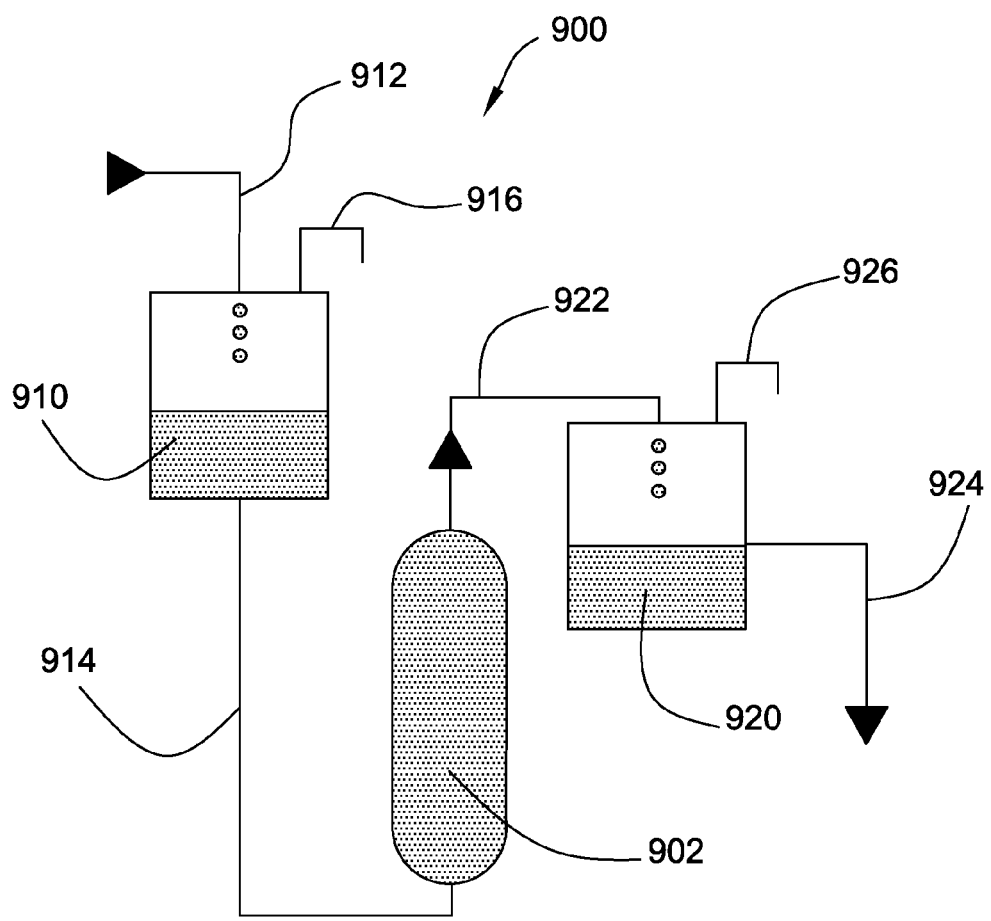
FIG. 12 is a general block diagram of a drip chamber system for electrically isolating fluid in the conductivity cell to reduce parasitic currents and current loss.

One mechanical solution to the problem of current leakage and parasitic currents is to physically isolate the fluid flowing into the conductivity cell from the rest of the fluid in the system by use of drip chambers. The drip chamber system 900 is generally represented in FIG. 12. In this design, fluid from the analytical process is directed to a first drip chamber 910 which can be any suitable size or volume. The fluid enters through inlet pipe 912 that includes an entrance orifice sized so that the fluid only drips into the interior of the first drip chamber 910. The dripping fluid can collect at the bottom of the first drip chamber 910 and, due to gravity induced pressure, can be directed from the bottom of the first drip chamber to the conductivity cell 902 via a first cell line 914. The conductivity cell 914 can include any of the above-mentioned C4D configurations and can employ the aforementioned four-wire resistance measurement method. The fluid enters the lower end of the conductivity cell 902 and is directed upwards through the cell to an exit at the top communicating with a second cell line 922. The second cell line 922 directs fluid to a second drip chamber 920 into which the fluid drips through an appropriately sized entrance orifice. The fluid is allowed to collect at the bottom of the second drip chamber 920 and can be returned to the process via a return line 924.

Because the fluid enters both the first drip chamber 910 and the second drip chamber 920 as discrete drops, the fluid directed through the conductivity cell 902 is electrically isolated from the rest of the fluid in the system. The dripping fluid is in contrast to a continuous stream that could form a closed conductor from the conductivity cell to the other fluid in the system. The drip chambers 910, 920 thereby reduce the presence of current leakage and parasitic currents in the fluid entering and exiting the conductivity cell 902. To facilitate continuous flow through the conductivity cell 902, the first drip chamber 910 is elevated above both the conductivity cell and the second line 922 and the entrance to the second drip chamber 920. Fluid collecting in the first drip chamber 910 thereby provides hydrostatic pressure to force itself through the conductivity cell 902 into the second drip chamber 920. To promote the hydrostatic pressure, the interiors of the first and second drip chambers 910, 920 can be vented to atmospheric pressure by first and second vents 916, 926 respectively. To restrict volume flow and promote the formation of droplets entering the drip chambers, the fluid communication lines can all have a narrow bore diameter. The use of narrow bore tubing to and from the conductivity cell also has been observed to provide some measure of electrical isolation of the conductivity cell from the system.

Figure 13:
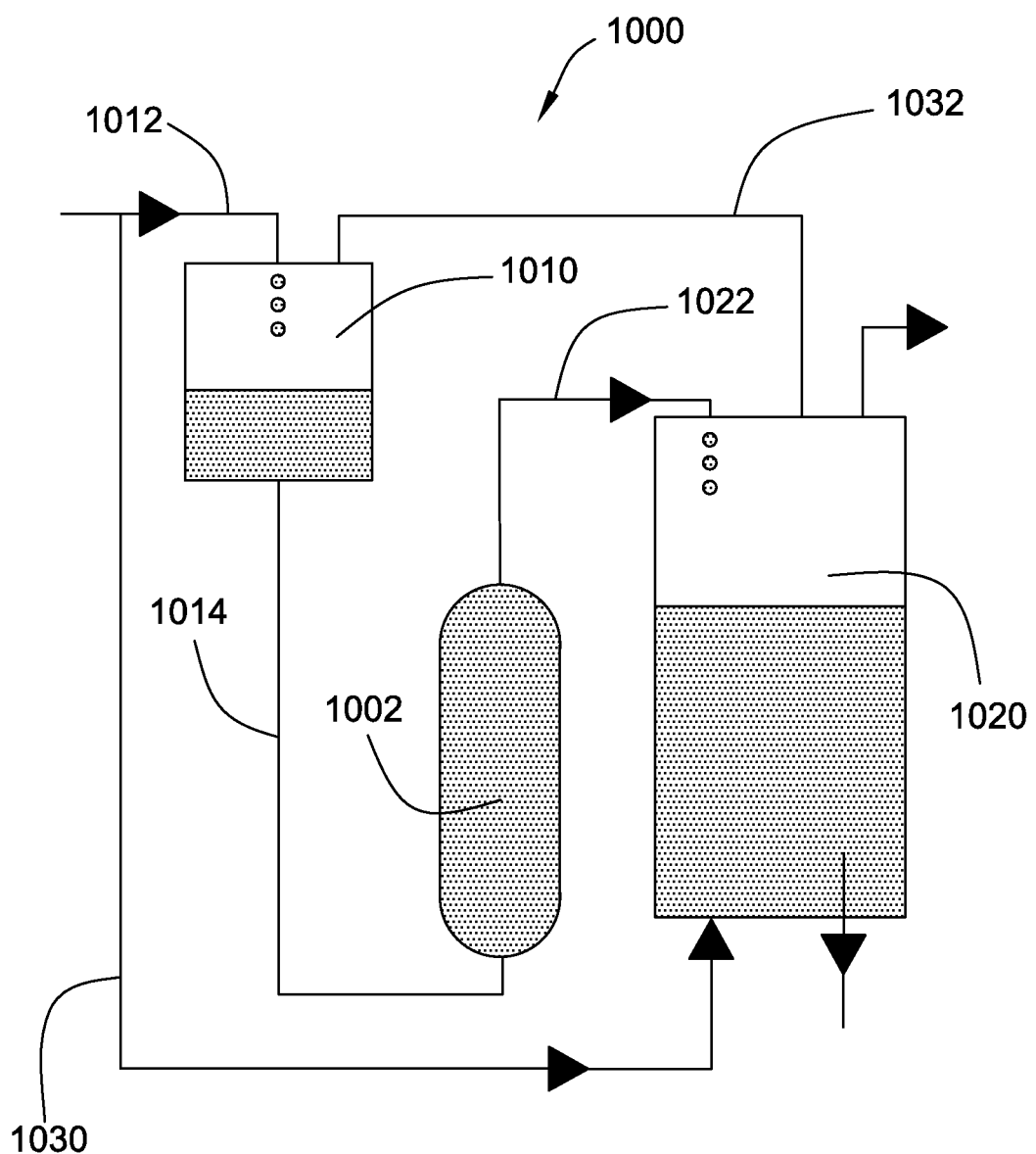
FIG. 13 is a general block diagram of another embodiment of a drip chamber system for isolating fluid in the conductivity cell to reduce parasitic currents and current loss.

Referring to FIG. 13, there is illustrated another embodiment of the drip chamber system 1000. The system 1000 includes a first drip chamber 1010 and a second drip chamber 1020 positioned upstream and downstream respectively of the conductivity cell 1002. To establish fluid communication, a first cell line 1014 leads from the first drip chamber 1010 to the conductivity cell 1002 and a second cell line 1022 leads from the conductivity cell to the second drip chamber 1020. The system 1000 also includes a bypass line 1030 that redirects fluid from an intake line 1012 around the first drip chamber 1010 and the conductivity cell 1002 to the second drip chamber 1020. Due to the bypass line 1030, at least a portion of the fluid bypasses the conductivity cell 1002 and will not undergo electrical analysis. The bypass line 1030 thereby helps further isolate and/or reduce parasitic currents and current leakage. The bypass line also allows for a greater volume of fluid to flow through the system than could otherwise be achieved using only the drip chambers. Another feature of the system is that the first and second drip chambers 1010, 1020 are connected via a pressure line 1032 so that both chambers are at the same internal pressure. Maintaining both drip chambers at the same internal pressure facilitates a continuous and steady fluid flow through the system. In other embodiments, the drip chambers may be pressurized or may be vented to atmospheric pressure.

Figure 14:
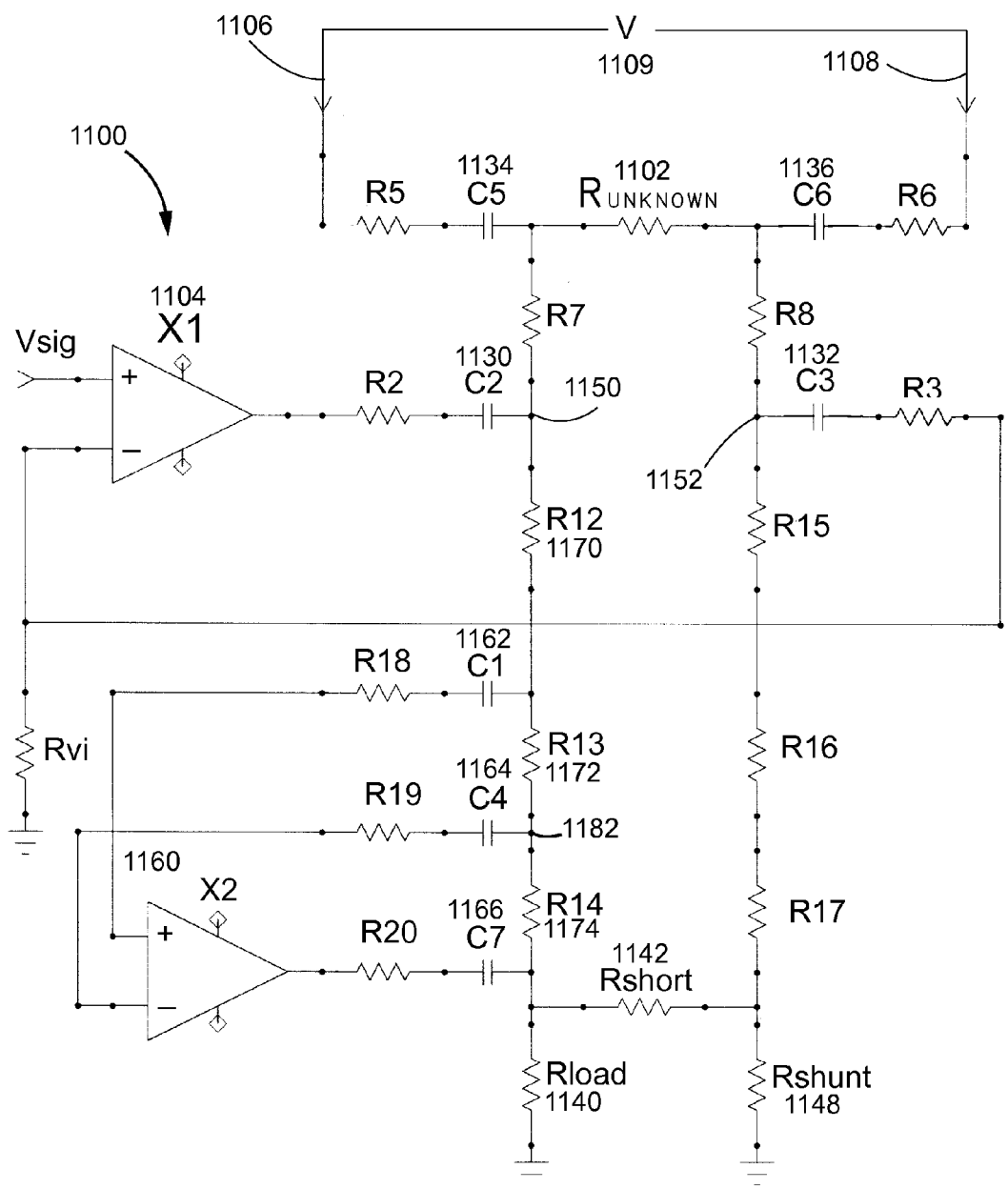
FIG. 14 is a schematic diagram of an electrical representation of a detector circuit for performing conductivity analysis including a counter circuit for reducing parasitic currents and current loss.

A second method of electrically isolating the conductivity cell is illustrated in FIG. 14 in which new features are added to the detector circuit 1100. FIG. 14 illustrates a power source such as an operational amplifier 1104 electrically connected to fluid in the conductivity cell represented by unknown resistance $R_{Unknown}$ 1102. To capacitively couple the power source 1104 to the conductivity cell 1102, the detector circuit includes a capacitor C2 1130 and capacitor C3 1132 which may be designed as excitation rings that surround the conductivity cell as described above. The voltmeter 1109 is coupled to the conductivity cell via first and second voltmeter leads 1106, 1008 that connect to capacitor C5 1134 and capacitor C6 1136 that represent the sense rings. As described with respect to FIG. 11, three resistors $R_{Load}$ 1140, $R_{Shunt}$ 1142, and $R_{Short}$ 1148 are illustrated that represent the current leakage or parasitic currents in the system, which typically result from the physical coupling between the excitation rings and the fluid in the conductivity cell.

A second power source, such as an operational amplifier 1160 is included with the detector circuit 1100 to eliminate the parasitic currents. Specifically, the second operational amplifier 1160 is coupled to the detector circuit 1100 via capacitors C1 1162, C4 1164 and C7 1166. Physically, capacitors C1 1162, C4 1164 and C7 1166 can be formed as electrode rings as described above that capacitively couple to the fluid in the conductivity cell. To establish that capacitive coupling, the capacitors C1 1162, C4 1164 and C7 1166 can be disposed about the conductivity cell, disposed about the fluid lines leading into and out of the conductivity cell or can be included with a second fluid chamber in fluid communication with the first fluid chamber of the cell. These capacitors may be formed by rings, the fluid, and the dielectric material of the fluid chamber in the same manner as the sense and excitation rings. As indicated in FIG. 14, the second operational amplifier 1160 communicates with the first and second nodes 1150, 1152 representing the coupling between the excitation rings and the fluid. The conductive path between the second operational amplifier 1160 and the first and second nodes 1150, 1152 includes a plurality of resistances R12 1170, R13 1172, and R14 1174, which represent electrical resistance from the fluid that capacitors C1 1162, C4 1164 and C7 1166 couples with.

The second operational amplifier 1160 can apply a voltage to node 1182, disposed between the parasitic currents represented by $R_{Load}$ 1140, $R_{Shunt}$ 1142, and $R_{Short}$ 1148 and the unknown resistance $R_{Unknown}$ 1102 representing the fluid in the conductivity cell. In particular, the voltage applied by the second operational amplifier 1160 to node 1182 via capacitor C7 1166 and resistance R14 1174 can be such that it makes the voltage across resistance R13 1172 becomes equal to zero, meaning no current can pass across the node. The parasitic currents represented by $R_{Load}$ 1140, $R_{Shunt}$ 1142, and $R_{Short}$ 1148 are thereby electrically isolated from the unknown resistance $R_{Unknown}$ 1102 representing the conductivity cell and have little effect on the detector circuit. The same technique may be applied to the components on the opposite side of FIG. 14.

Figure 15:
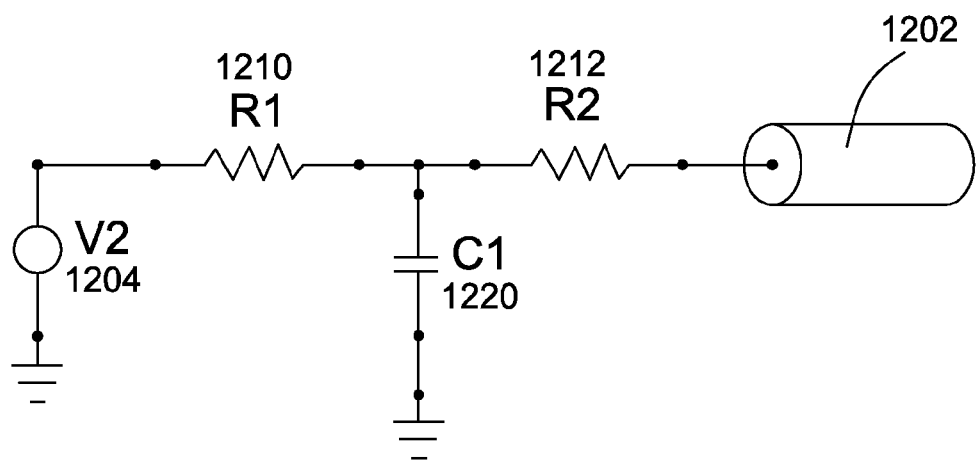
FIG. 15 is a schematic diagram of an electrical representation of the detector circuit for performing conductivity analysis including passive isolator for isolating parasitic currents and current loss.
Figure 16:
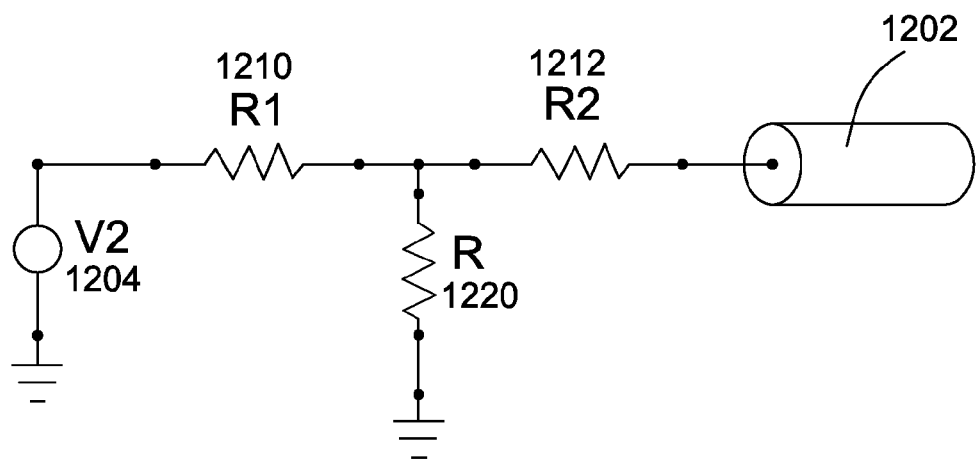
FIG. 16 is another schematic diagram of an electrical representation of the detector circuit for performing conductivity analysis including another type of passive isolator.

Referring to FIGS. 15 and 16, there is illustrated another embodiment of a method of electrically isolating fluid flowing into the conductivity cell from other EMI in the system that may create errors with the conductivity cell readings. In this embodiment, in which physical components are represented by electrical components, the power source 1204, an EMI or other noise source, is electrically coupled to the conductivity cell 1202 via the fluid. Resistors R1 1210 and R2 1212 represent lengths of narrow bore tubing that direct fluid from the process to the conductivity cell 1202. Resistors R1 1210 and R2 1212 also represent leakage paths from the conductivity cell 1202 to the ground by which current is diverted or shunted away from the conductivity cell. To reduce the error caused by the leakage paths represented by resistors R1 1210 and R2 1212, a new electrical component such as a capacitor or a resistor that provides a passive isolator 1220 can be connected to the circuit as illustrated. For example, if a capacitor is used for the passive isolator 1220, it can be constructed in accordance with the electrode ring design disclosed above. As illustrated in FIG. 16, if a resistor is used for the passive isolator 1220, it can be directly connected to the ground. An example would be a length of grounded stainless steel tubing, in which case, R 1220 is very small making the isolator very effective. It has been observed that inclusion of the passive isolator 1220 helps reduce error in conductivity cell measurements that arise from the presence of other EMI in the system.

Self-Calibration of the Detector Circuit

Figure 17:
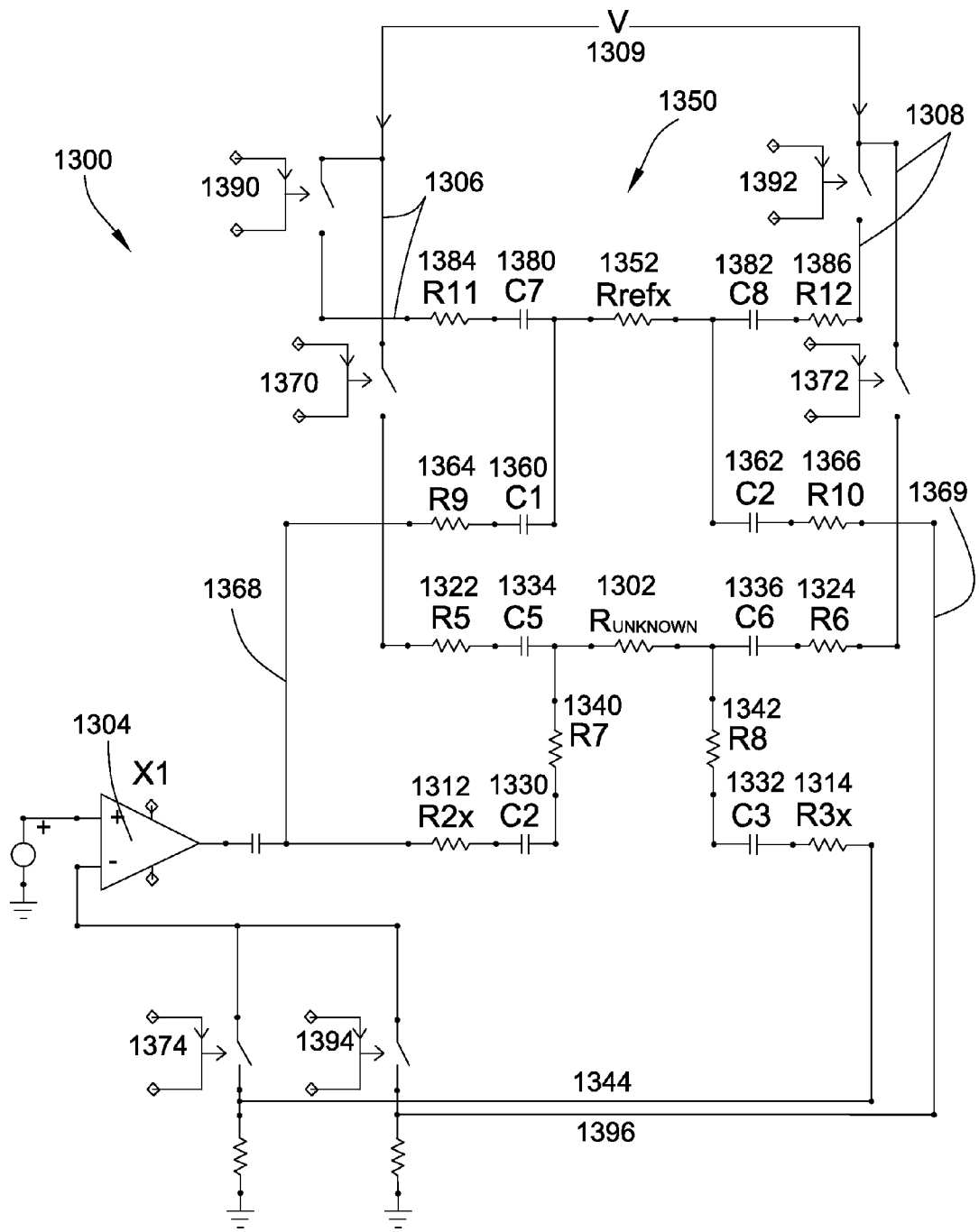
FIG. 17 is a schematic diagram of an electrical representation of the detector circuit for performing conductivity analysis including a calibration portion for calibrating and reducing errors in conductivity measurement.

To further reduce errors and improve conductivity sensing accuracy, there is illustrated in FIG. 17 an embodiment of a detector circuit 1300 configured to at least partially calibrate itself. The detector circuit 1300 includes a fluid of unknown conductivity disposed in a conductivity cell represented as an unknown resistance $R_{Unknown}$ 1302. To supply current for measuring the conductivity of the unknown resistance $R_{Unknown}$ 1302, a power source 1304 is coupled to the fluid in the conductivity cell via excitation electrodes represented as capacitances C2 1330 and C3 1332. Resistances R2 1312 and R3 1314 represent the resistance associated with the leads and electrodes connecting the power source 1304 to the conductivity cell and resistances R7 1340 and R8 1342 represent the resistance associated with the fluid between the excitation and sense rings. A voltmeter 1309 can be selectively coupled to the unknown resistance $R_{Unknown}$ 1302 representing the conductivity cell via sense electrodes represented as capacitances C5 1334 and C6 1336 and resistances R5 1322 and R6 1324 that represent the resistance associated with the leads and the electrodes. To enable selective coupling of the voltmeter 1309 and the unknown resistance $R_{Unknown}$ 1302, a first switch or relay 1370 is disposed along the first voltmeter line 1306 and a second switch or relay 1372 is disposed along the second voltmeter line 1308. A third relay 1374 is included in the circuit along the return line 1344 from the unknown resistance $R_{Unknown}$ 1302 to facilitate selective coupling with the power source 1304. Opening and closing the relays 1370, 1372 establishes communication between the unknown resistance $R_{Unknown}$ 1302 and the rest of the detector circuit 1300. Any suitable type of current source could be used and any method of selecting the current source employed.

To provide a reference against which the detector circuit 1300 can calibrate itself, the basic circuitry is duplicated in large part toward the top half of FIG. 17 by a calibration portion 1350. The calibration portion 1350 of the detector circuit 1300 includes a reference resistor $R_{ref}$ 1352 of a predetermined value and which is arranged in the circuit to approximately replicate the unknown resistance $R_{Unknown}$ 1302. The reference resistor $R_{ref}$ 1352 can also be connected to the power source 1304 by capacitor C1 1360 and capacitor C2 1362. The leads 1368, 1369 from the power source 1304 to the reference resistor $R_{ref}$ 1352 bypass the portion of the detector circuit that includes the resistances and capacitances associated with the unknown resistance $R_{Unknown}$ 1302. To represent the resistance associated with the leads and terminals to reference resistor $R_{ref}$ 1352, resistors R9 1364 and R10 1366 are shown in series with capacitors C1 1360 and C2 1362 respectively. The reference resistor $R_{ref}$ 1350 can be selectively coupled with the meter leads 1306, 1308 to the voltmeter 1309 by communicating through capacitor C7 1380 and capacitor C8 1382 and resistors R11 1384 and resistor R12 1386. To enable selective coupling of the reference resistor $R_{ref}$ 1350, fourth and fifth switches or relays 1390, 1392 are disposed in series between the reference resistor $R_{ref}$ and the voltmeter. A sixth relay 1394 is also disposed along the return line 1396 to the power source 1304 to selectively couple the reference resistor $R_{ref}$ 1352 with the power source. Any suitable type of current source may be used with the circuit and any suitable method for selecting the current source falls within the scope of the disclosure. In certain cases, it may be advantageous to drive both the detector cell and the reference portion to reduce relative voltage differences across the switch or relay contacts to reduce parasitic currents.

In operation, the first, second and third relays 1370, 1372, 1374 may be opened and closed in an alternate manner with respect to the fourth, fifth and sixth relays 1390, 1392, 1394 to selectively couple the either the unknown resistance $R_{Unknown}$ 1302 or the reference resistor $R_{ref}$ 1350 with the power supply 1304 and the voltmeter 1309. Hence, the voltmeter 1309 can alternatively receive signals from either the unknown resistance $R_{Unknown}$ 1302 or the reference resistance $R_{ref}$ 1352. By comparing the signal from the unknown resistance $R_{Unknown}$ 1302 corresponding to the fluid in the conductivity cell with the signal from the reference resistor $R_{ref}$ 1350, the detector circuit 1300 may factor out certain errors and discrepancies. For example, the power source 1304 may develop errors or drift over time due to aging, temperature effects or other reasons. The voltmeter 1309 may develop similar issues. Errors in the circuitry can be factored out by alternately referencing the unknown resistance $R_{Unknown}$ 1302 and the reference resistor $R_{ref}$ 1352. The reason for the reference portion 1350 is thus to emulate that electrical response of the real conductivity cell, thus tending to induce the same errors and magnitude of error in the power source and meter circuit. The detector circuit 1300 thereby provides a self-calibrating function enabling it to periodically correct itself. Other analytical equipment operating in conjunction with the voltmeter 1309 can also utilize the calibration function. Although in the present embodiment, the calibration portion of the detector circuit 1300 is described as being comprised of electrical components, it will be appreciated that in other embodiments the calibration portion can instead include a conductivity cell as described above in which is disposed a reference fluid of a known conductivity.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A conductivity detector for measuring the conductivity of a fluid comprising:
   an elongated hollow fluid chamber delineating an interior channel, the hollow chamber including a first end and a second end, the first end being open for receiving a fluid into the interior channel;
   a first excitation electrode disposed proximate the first end of the hollow chamber and a second excitation electrode disposed proximate the second end of the hollow chamber;
   a first sense electrode and a second sense electrode, the first and second sense electrodes disposed between the first and second excitation electrodes;
   a power source communicating with the first and second excitation electrodes; and
   a meter communicating with the first and second sense electrodes;
   wherein current from the power source applied to the first and second excitation electrodes induces current in the fluid received in the interior channel by capacitively coupling with the fluid, the induced current being sensed by the first and second sense electrodes by capacitively coupling the first and second sense electrodes with the fluid.

2. The conductivity detector of claim 1, wherein the fluid chamber is generally cylindrical and delineates an axis line.

3. The conductivity detector of claim 2, wherein the first sense electrode and the second sense electrode are axially spaced from each other by a first distance.

4. The conductivity detector of claim 3, wherein the first excitation electrode and the second excitation electrode are axially spaced from each other by a second distance, the second distance larger than the first distance.

5. The conductivity detector of claim 1, wherein the first and second excitation electrodes are respective first and second excitation rings having an annular shape, and the first and second sense electrodes are respective first and second sense rings each having an annular shape.

6. The conductivity detector of claim 1, wherein the fluid chamber is a disposable component.

7. The conductivity detector of claim 6, wherein the fluid chamber is slidably received through the annular shaped first and second excitation rings and the annular shaped first and second sense rings.

8. The conductivity detector of claim 6, further comprising a casing, the fluid chamber removably accommodated in the casing.

9. The conductivity detector of claim 8, wherein the casing includes a cavity disposed therein, the cavity having a shape corresponding the fluid chamber.

10. The conductivity detector of claim 9, wherein the fluid chamber has a flexible characteristic, and the cavity and the fluid chamber form an interference fit to shape the fluid chamber to the cavity.

11. The conductivity detector of claim 8, wherein the first and second excitation electrodes and the first and second sense electrodes are locationally fixed relative to the fluid chamber by the casing.

12. The conductivity detector of claim 11, wherein the casing includes isolators to space apart and electrically isolate the first and second excitation rings and the first and second sense rings.

13. The conductivity detector of claim 8, wherein the casing includes a first half and a second half movable together to close and open the casing, for removing and disposing of the fluid chamber.

14. The conductivity detector of claim 8, wherein the casing includes a window disposed therein for infrared thermal measurement of the fluid.

15. The conductivity detector of claim 1, wherein the first and second excitation electrodes are disposed in the fluid chamber and exposed to interior channel, and the first and second sense electrodes are disposed in the fluid chamber and exposed to the interior channel.

16. The conductivity detector of claim 1, further comprising a first drip chamber located upstream of the fluid chamber and a second drip chamber located downstream of the fluid chamber.

17. The conductivity detector of claim 1, further comprising a calibration portion including a reference resistor that can selectively couple to the power source and the meter.

18. A conductivity cell for measuring the conductivity of a fluid comprising:
   an elongated, disposable fluid chamber having a first end and a second end, the fluid chamber being hollow and delineating an interior channel for receiving the fluid;
   a first excitation ring disposed about the exterior of the fluid chamber proximate the first end configured to capacitively couple with the fluid received in the interior channel;
   a second excitation ring disposed about the exterior of the fluid chamber proximate the second end configured to capacitively couple with the fluid received in the interior channel;
   a first sense ring and a second sense ring disposed about the exterior of the fluid chamber between the first and second excitation rings, the first and second sense rings configured to capacitively couple with the fluid received in the interior channel;

whereby the fluid chamber is removable from the first and second excitation rings and the first and second sense rings for disposal and replacement.

19. The conductivity cell of claim 18, wherein the fluid chamber is cylindrical and the first and second excitation rings and the first and second sense rings are annular.

20. The conductivity cell of claim 18, wherein the fluid chamber comprises polyvinyl chloride.

* * * * *